(12) United States Patent
Nishijima et al.

(10) Patent No.: US 10,371,829 B2
(45) Date of Patent: Aug. 6, 2019

(54) X-RAY DETECTOR AND X-RAY CT APPARATUS

(71) Applicant: Canon Medical Systems Corporation, Otawara-shi (JP)

(72) Inventors: Akira Nishijima, Nasushiobara (JP); Michito Nakayama, Utsunomiya (JP); Atsushi Hashimoto, Otawara (JP); Takaya Umehara, Kawasaki (JP); Shuya Nambu, Nasushiobara (JP); Hiroaki Miyazaki, Otawara (JP)

(73) Assignee: Canon Medical Systems Corporation, Otawara-shi (JP)

( * ) Notice: Subject to any disclaimer, the term of this patent is extended or adjusted under 35 U.S.C. 154(b) by 58 days.

(21) Appl. No.: 15/332,118

(22) Filed: Oct. 24, 2016

(65) Prior Publication Data

US 2017/0205517 A1  Jul. 20, 2017

(30) Foreign Application Priority Data

Jan. 20, 2016  (JP) .................................. 2016-009001

(51) Int. Cl.
*G01T 1/20* (2006.01)
*A61B 6/03* (2006.01)
*H01L 27/146* (2006.01)

(52) U.S. Cl.
CPC ............ *G01T 1/2018* (2013.01); *A61B 6/032* (2013.01); *H01L 27/14659* (2013.01)

(58) Field of Classification Search
CPC ............................ A61B 6/4233; G01T 1/2018
See application file for complete search history.

(56) References Cited

U.S. PATENT DOCUMENTS

| 6,243,438 | B1 * | 6/2001 | Nahaliel | A61B 6/032 378/19 |
|---|---|---|---|---|
| 2013/0230134 | A1 * | 9/2013 | Li | A61B 6/032 378/20 |
| 2016/0029982 | A1 * | 2/2016 | Tamura | G01T 1/2018 378/19 |

FOREIGN PATENT DOCUMENTS

| JP | 2009-118943 | 6/2009 |
|---|---|---|
| JP | 2016-32491 | 3/2016 |

\* cited by examiner

*Primary Examiner* — Hoon K Song
(74) *Attorney, Agent, or Firm* — Oblon, McClelland, Maier & Neustadt, L.L.P.

(57) ABSTRACT

An X-ray detector according to an embodiment includes a scintillator array and a photodiode array. In the scintillator array, a plurality of scintillators are arranged in a first direction and a second direction intersecting the first direction. The photodiode array includes photodiodes each of which is installed for a different one of the scintillators and each of which has an active area configured to convert visible light emitted by the scintillator into an electrical signal. The photodiodes are arranged in such a manner that the widths of the active areas are equal to one another in the first direction.

3 Claims, 13 Drawing Sheets

US 10,371,829 B2

X-RAY DETECTOR AND X-RAY CT APPARATUS

CROSS-REFERENCE TO RELATED APPLICATIONS

This application is based upon and claims the benefit of priority from Japanese Patent Application No. 2016-009001, filed on Jan. 20, 2016; the entire contents of which are incorporated herein by reference.

FIELD

Embodiments described herein relate generally to an X-ray detector and an X-ray CT apparatus.

BACKGROUND

An X-ray detector included in a conventional X-ray Computed Tomography (CT) apparatus includes a photodiode array in which a plurality of active areas are formed. To uniformly detect X-rays radiated by an X-ray tube, the active areas are arranged at regular intervals. In this situation, the expression "intervals between the active areas" denotes the intervals recognised when the conventional X-ray CT apparatus reconstructs projection data.

The photodiode array is manufactured by cutting out silicon wafer having the active areas formed on a surface thereof. During the process of cutting out the silicon wafer however, very small cracks may occur in end parts of the silicon wafer. Further, in the surrounding areas of the active areas, for example, wirings for circuitry configured to detect X-rays are installed. For this reason, the photodiode array includes one or more active-area formation prohibited areas.

Accordingly, the active areas positioned closest to the end parts of the photodiode array are smaller than the other active areas. For this reason, the detection efficiency levels or the signal-to-noise (SN) ratios of the photodiodes having the active areas positioned closest to the end parts of the photodiode array may be degraded. Further, an artifact may occur due to the degradation of the detection efficiency levels and/or the SN ratios of the photodiodes.

DETAILED DESCRIPTION

An X-ray detector according to an embodiment includes a scintillator array and a photodiode array. In the scintillator array, a plurality of scintillators are arranged in a first direction and a second direction intersecting the first direction. The photodiode array includes photodiodes each of which is installed for a different one of the scintillators and each of which has an active area configured to convert visible light emitted by the scintillator into an electrical signal. The photodiodes are arranged in such a manner that the widths of the active areas are equal to one another in the first direction.

Exemplary embodiments of an X-ray detector and an X-ray CT apparatus will be explained below, with reference to the accompanying drawings. In the embodiments described below, duplicate explanations will be omitted, as appropriate.

First Embodiment

Figure 1:
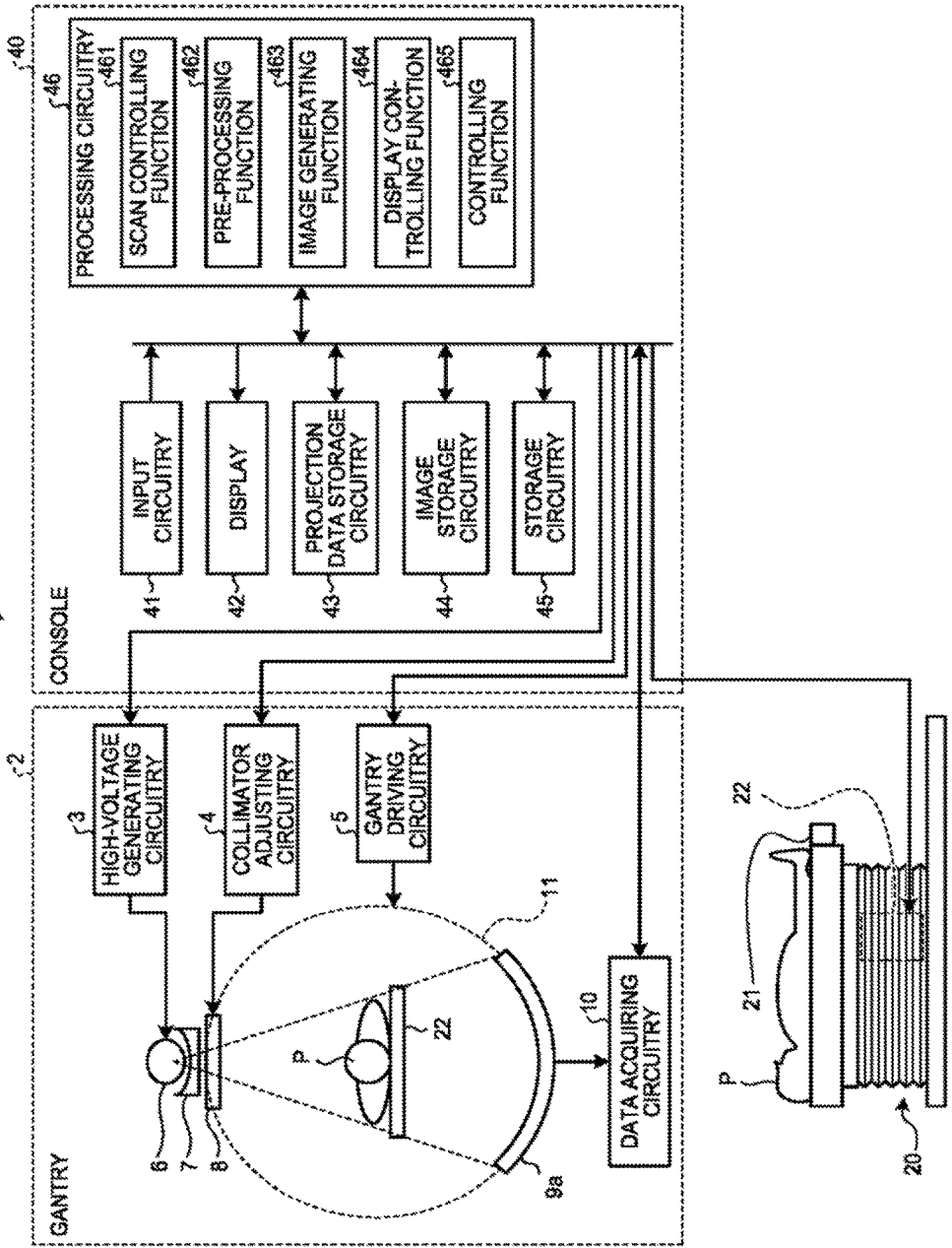
FIG. 1 is a diagram of an exemplary configuration of an X-ray CT apparatus according to a first embodiment.

A configuration of an X-ray CT apparatus 1 according to a first embodiment will be explained, with reference to FIG. 1. FIG. 1 is a diagram of an exemplary configuration of the X-ray CT apparatus according to the first embodiment. As illustrated in FIG. 1, the X-ray CT apparatus 1 includes gantry 2, a couch 20, and a console 40. Possible configurations of the X-ray CT apparatus 1 are not limited to the configuration described below.

The gantry 2 includes high-voltage generating circuitry 3, collimator adjusting circuitry 4, gantry driving circuitry 5, an X-ray tube 6, a wedge 7, a collimator 8, an X-ray detector 9a, data acquiring circuitry 10, and a rotating frame 11.

The high-voltage generating circuitry 3 is configured to supply an X-ray tube voltage to the X-ray tube 6 explained later. The collimator adjusting circuitry 4 is configured to adjust the radiation range of X-rays generated by the X-ray tube 6, by adjusting the opening degree and the position of the collimator 8. The gantry driving circuitry 5 is configured to rotate the rotating frame 11. The gantry driving circuitry 5 thereby causes the X-ray tube 6 and the X-ray detector 9a to turn on a circular trajectory centered on an examined subject P. Further, the high-voltage generating circuitry 3, the collimator adjusting circuitry 4, and the gantry driving circuitry 5 are realized by means of a processor, for example.

The X-ray tube 6 is configured to radiate X-rays onto the patient P. The X-ray tube 6 is configured to generate the X-rays by using the X-ray tube voltage supplied thereto by the high-voltage generating circuitry 3. The wedge 7 is an X-ray filter configured to adjust the dose of the X-rays radiated onto the subject P. The collimator 8 is a slit configured to adjust the radiation range of the X-rays radiated onto the subject P.

The X-ray detector 9a is configured to detect the X-rays radiated by the X-ray tube 6. The X-ray detector 9a includes scintillator arrays 91 and photodiode arrays 92a. Each of the scintillator arrays 91 includes a plurality of scintillators arranged in a first direction and a second direction intersecting the first direction. In the present example, the first direction is the circumferential direction of the rotating frame 11, for example, whereas the second direction is the body axis direction of the subject P, for example. The first direction and the second direction do not necessarily have to be orthogonal to each other. Each of the scintillators is configured to convert X-rays that have become incident thereto into visible light. Each of the photodiode arrays 92a includes photodiodes each of which is installed for a different one of the scintillators. Each of the photodiodes has an active area configured to convert visible light emitted by the scintillator into an electrical signal. The electrical signal is transmitted to the data acquiring circuitry 10 explained later.

Further, the photodiodes are arranged in such a manner that, in at least one selected from between the first direction and the second direction, the difference in the width between any two of the active areas positioned adjacent to each other is within a predetermined range and that the intervals between the pairs of adjacently-positioned active areas exhibit multiple values. Entails of the X-ray detector 9a will be explained later. The active areas may also be referred to as anodes.

The data acquiring circuitry 10 is configured to generate projection data on the basis of the electrical signals output by the photodiodes. The projection data may represent a sinogram, for example. The sinogram is represented by data in which the signals detected by the photodiodes in the corresponding positions of the X-ray tube 6 are arranged in a formation. In this situation, the position of the X-ray tube 6 is called a view. The sinogram is represented by data in which effective energy levels of the X-rays detected by the photodiodes are assigned to a two-dimensional Cartesian coordinate system of which the axes extend in the view direction and the channel direction. The data acquiring circuitry 10 stores the generated sinogram into projection data storage circuitry 43 explained later. The data acquiring circuitry 10 is included in a Data Acquisition System (DAS). Further, the data acquiring circuitry 10 is realized by means of a processor, for example.

The rotating frame 11 is an annular frame. The rotating frame 11 is configured to support the X-ray tube 6 and the X-ray detector 9a so as to oppose each other. The rotating frame 11 is driven by the gantry driving circuitry 5 and is configured to rotate while being centered on the subject P.

The couch 20 includes a couchtop 21 and couch driving circuitry 22. The couchtop 21 is a plate-like member on which the subject P is placed. The couch driving circuitry 22 is configured to move the subject P within an image taking opening of the gantry 2 by moving the couchtop 21 on which the subject P is placed. Further, the couch driving circuitry 22 is realized by means of a processor, for example.

The console 40 includes input circuitry 41, a display 42, the projection data storage circuitry 43, image storage circuitry 44, storage circuitry 45, and processing circuitry 46.

The input circuitry 41 is used by a user who inputs instructions and settings. The input circuitry 41 may be included in a mouse and/or a keyboard, for example. The input circuitry 41 is configured to transfer the instructions and the settings input by the user, to the processing circuitry 46. The input circuitry 41 is realized by means of a processor, for example.

The display 42 is a monitor referenced by the user. The display 42 is configured to receive, from the processing circuitry 46, an instruction indicating that, for example, a CT image or a Graphical User Interface (GUI) used by the user when inputting an instruction or a setting should be displayed. On the basis of the instruction, the display 42 displays the CT image or the GUI.

The projection data storage circuitry 43 is configured to store therein the projection data generated by the data acquiring circuitry 10 and raw data generated by a pre-processing function 462 explained later. The image storage circuitry 44 is configured to store therein a CT image generated by an image generating function 463 explained later.

The storage circuitry 45 stores therein a computer program (hereinafter, "program") used by the high-voltage generating circuitry 3, the collimator adjusting circuitry 4, the gantry driving circuitry 5, and the data acquiring circuitry 10 to realize the functions described above. The storage circuitry 45 stores therein a program used by the couch driving circuitry 22 to realize the functions described above. The storage circuitry 45 stores therein a program used by the processing circuitry 46 to realize the functions such as a scan controlling function 461, the pre-processing function 462, the image generating function 463, a display controlling function 464, a controlling function 465, and other functions. Accordingly, the high-voltage generating circuitry 3, the collimator adjusting circuitry 4, the gantry driving circuitry 5, the data acquiring circuitry 10, the couch driving circuitry 22, and the processing circuitry 46 realize the functions thereof by reading and executing the programs stored in the storage circuitry 45.

Further, the projection data storage circuitry 43, the image storage circuitry 44, and the storage circuitry 45 include one or more storage media from which a computer is able to read the information stored therein. The storage media may each be a hard disk, for example.

The processing circuitry 46 includes the scan controlling function 461, the pre-processing function 462, the image generating function 463, the display controlling function 464, and the controlling function 465. Details of these functions will be explained later. The processing circuitry 46 is realized by means of a processor, for example.

Figure 2:
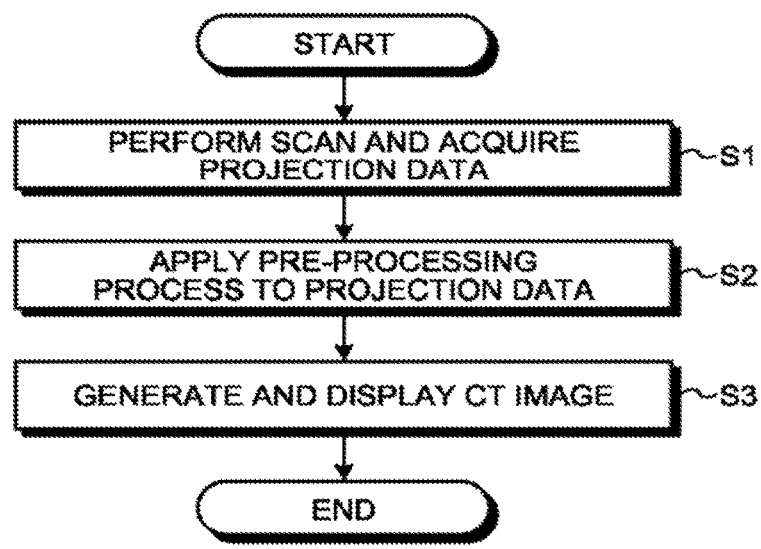
FIG. 2 is a flowchart illustrating an example of a process performed by the X-ray CT apparatus according to the first embodiment.

An example of a process performed by the X-ray CT apparatus 1 according to the first embodiment will be explained, with reference to FIG. 2. FIG. 2 is a flowchart illustrating the example of the process performed by the X-ray CT apparatus according to the first embodiment.

As illustrated in FIG. 2, the processing circuitry 46 performs a scan and acquires projection data (step S1). The process at step S1 can be explained as follows, for example:

The processing circuitry 46 reads and executes the program corresponding to the scan controlling function 461 from the storage circuitry 45. The scan controlling function 461 is a function configured to control the X-ray CT apparatus 1 to perform the scan. For example, by executing the scan controlling function 461, the processing circuitry 46 controls the X-ray CT apparatus 1 in the following manner:

The processing circuitry 46 moves the subject P to the inside of the image taking opening of the gantry 2, by controlling the couch driving circuitry 22. The processing circuitry 46 causes the gantry 2 to perform the scan on the subject P. More specifically, the processing circuitry 46 causes the X-ray tube voltage to be supplied to the X-ray tube 6, by controlling the high-voltage generating circuitry 3. The processing circuitry 46 adjusts the opening degree and the position of the collimator 8 by controlling the collimator adjusting circuitry 4. Further, the processing circuitry 46 causes the rotating frame 11 to rotate, by controlling the gantry driving circuitry 5. After that, the processing circuitry 46 causes the data acquiring circuitry 10 to acquire projection data, by controlling the data acquiring circuitry 10. The scan performed by the X-ray CT apparatus 1 may be, for example, a conventional scan, a helical scan, or a step-and-shoot scan.

As illustrated in FIG. 2, the processing circuitry 46 applies a pre-processing process to the projection data (step S2). The process at step S2 can be explained as follows, for example:

The processing circuitry 46 reads and executes the program corresponding to the pre-processing function 462 from the storage circuitry 45. The pre-processing function 462 is a function configured to correct the projection data generated by the data acquiring circuitry 10. The correction may be, for example, a logarithmic transformation, an offset correction, a sensitivity correction, a beam hardening correction, and/or a scattered ray correction. The projection data corrected by the pre-processing function 462 is stored into the projection data storage circuitry 43. The projection data corrected by the pre-processing function 462 may be referred to as raw data.

As illustrated in FIG. 2, the processing circuitry 46 generates and displays a CT image (step S3). The process at step S3 can be explained as follows, for example:

The processing circuitry 46 reads and executes the program corresponding to the image generating function 463 from the storage circuitry 45. The image generating function 463 is a function configured to reconstruct the raw data stored in the projection data storage circuitry 43 and to generate a CT image. For example, the reconstruction method may be implemented as a back projection process or may be an iterative approximation method. The processing circuitry 46 reads and executes the program corresponding to the display controlling function 464 from the storage circuitry 45. The display controlling function 464 is a function configured to cause the display 42 to display the CT image stored in the image storage circuitry 44.

When performing the processes explained above, the processing circuitry 46 reads and executes the program corresponding to the controlling function 465 from the storage circuitry 45, as appropriate. The controlling function 465 includes, among others, a function of bringing the constituent elements of the gantry 2, the couch 20, and the console 40 into operation with appropriate timing in accordance with purposes.

Figure 3:
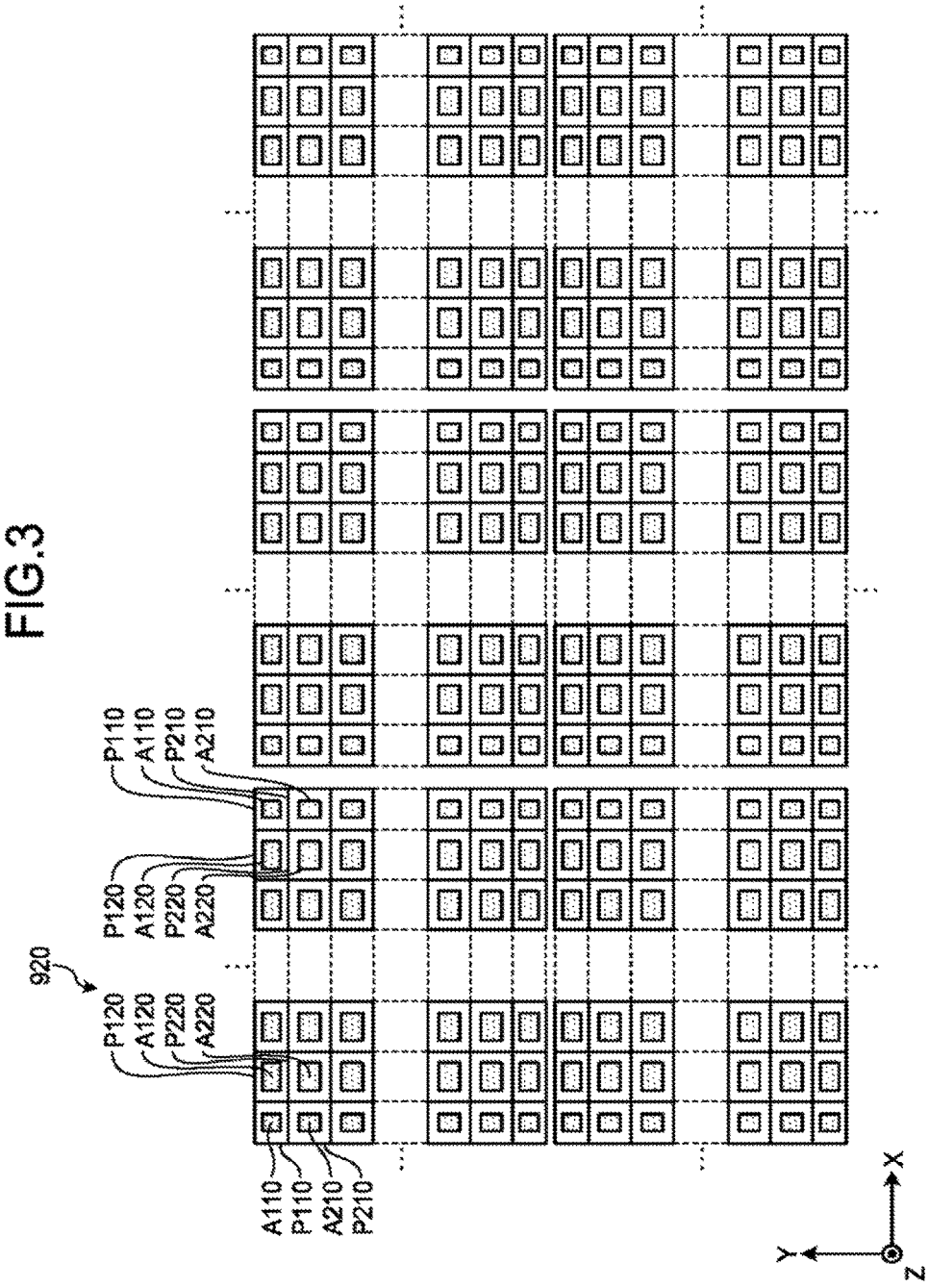
FIG. 3 is a drawing illustrating an example of positional arrangements of photodiodes and active areas included in a conventional X-ray detector.
Figure 4:
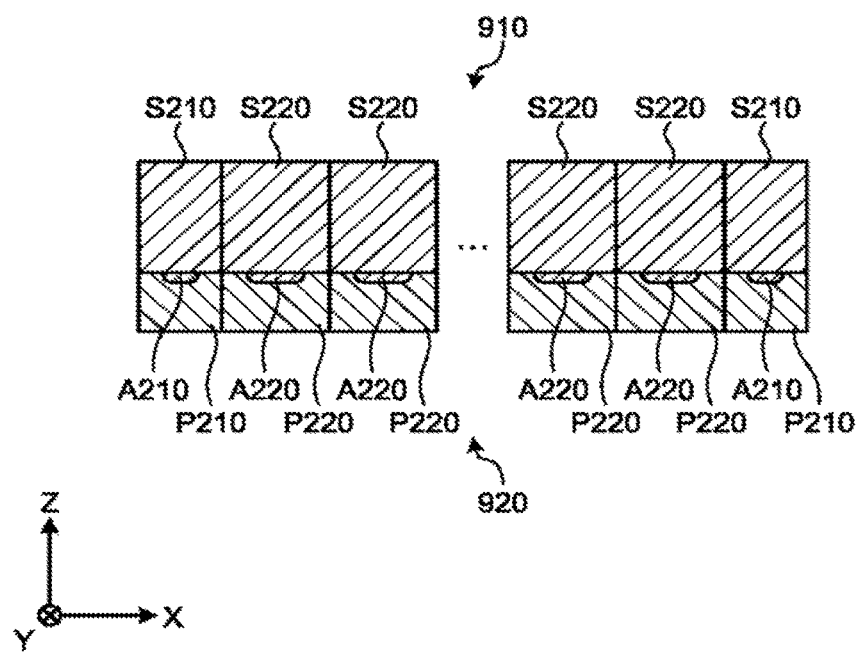
FIG. 4 is a cross-sectional view of one of the photodiode arrays illustrated in FIG. 3 and a scintillator array positioned on a +Z direction side of the photodiode array, being cross-sectioned by a plane that passes through active areas and is positioned parallel to a Z-X plane and being viewed from a −Y direction.
Figure 5:
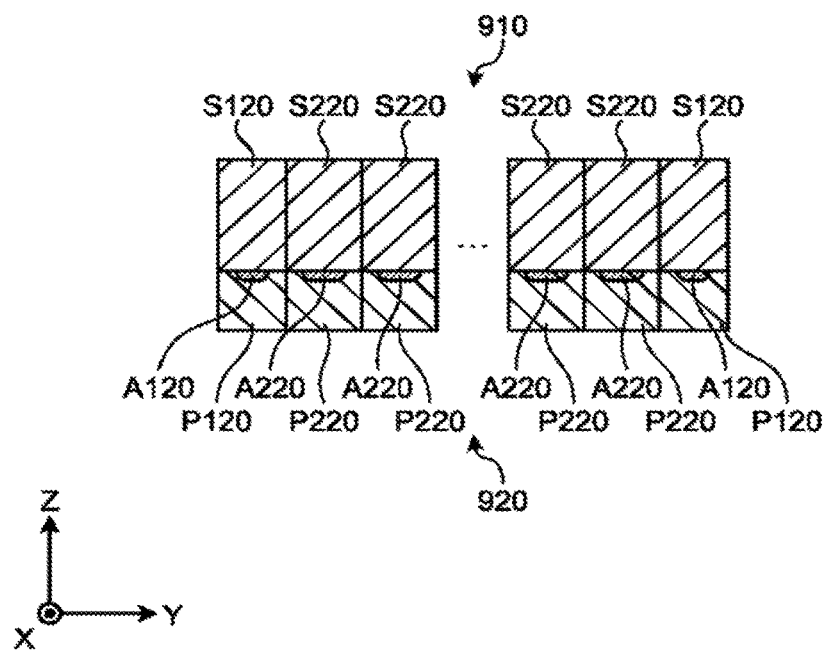
FIG. 5 is a cross-sectional view of the one of the photodiode arrays illustrated in FIG. 3 and the scintillator array positioned on the +Z direction side of the photodiode array, being cross-sectioned by a plane that passes through active areas and is positioned parallel to a Y-Z plane and being viewed from a +X direction.

Next, to make it easier to understand configurations of the X-ray detectors according to the first to the fifth embodiments explained later, an example of a conventional X-ray detector and problems thereof will be explained, with reference to FIGS. 3, 4, and 5. FIG. 3 is a drawing illustrating an example of positional arrangements of photodiodes and active areas included in a conventional X-ray detector. FIG. 4 is a cross-sectional view of one of the photodiode arrays illustrated in FIG. 3 and a scintillator array positioned on the +Z direction side of the photodiode array, being cross-sectioned by a plane that passes through active areas and is positioned parallel to a Z-X plane and being viewed from a −Y direction. FIG. 5 is a cross-sectional view of the one of the photodiode arrays illustrated in FIG. 3 and the scintillator array positioned on the +Z direction side of the photodiode array, being cross-sectioned by a plane that passes through active areas and is positioned parallel to a Y-Z plane and being viewed from the +X direction.

In the following explanations, an X-direction, a Y-direction, and a Z-direction defined as follows will be used. The circumferential direction of the rotating frame 11 will be defined as the X-direction. The body axis direction of the subject P will be defined as the Y-direction. The direction orthogonal to the X-direction and the Y-direction will be defined as the Z-direction.

As illustrated in FIG. 3, in the conventional X-ray detector, photodiode arrays 920 are arranged at certain intervals in the X-direction and the Y-direction.

As illustrated in FIG. 3, each of the photodiode arrays 920 includes four photodiodes P110, a plurality of photodiodes P120, a plurality of photodiodes P210, and a plurality of photodiodes P220. When being viewed from the direction perpendicular to the detection surface of the X-ray detector, each of the photodiodes P110, the photodiodes P120, the photodiodes P210, and the photodiodes P220 is in the shape of a rectangle of which one pair of opposing sides extends parallel to the X-direction and of which the other pair of opposing side extends parallel to the Y-direction.

The width of each of the photodiodes P110 in the X-direction is equal to the width of each of the photodiodes P210 in the X-direction. The width of each of the photodiodes P120 in the X-direction is equal to the width of each of the photodiodes P220 in the X-direction. The width of each of the photodiodes P110 in the X-direction is smaller than the width of each of the photodiodes P120 in the X-direction.

The width of each of the photodiodes P110 in the Y-direction is equal to the width of each of the photodiodes P120 in the Y-direction. The width of each of the photodiodes P210 in the Y-direction is equal to the width of each of the photodiodes P220 in the Y-direction. The width of each of the photodiodes P110 in the Y-direction is smaller than the width of each of the photodiodes P210 in the Y-direction.

The photodiodes P110 are positioned in the four corners of each of the photodiode arrays 920. The photodiodes P120 are positioned in the two end parts, in terms of the Y-direction, of each of the photodiode arrays 920 and are arranged along the X-direction. The photodiodes P210 are positioned in the two end parts, in terms of the X-direction, of each of the photodiode arrays 920 and are arranged along the Y-direction. The photodiodes P220 are arranged in a matrix formation in the region surrounded by the photodiodes P110, the photodiodes P120, and the photodiodes P210. The photodiodes P110, the photodiodes P120, the photodiodes P210, and the photodiode P210 correspond to the pixels in each of the views of the projection data described above.

As illustrated in FIG. 3, each of the photodiodes P110 has an active area A110. Each of the photodiodes P120 has an active area A120. Each of the photodiodes P210 has an active area A210. Each of the photodiodes P220 has an active area A220. The active areas A110, the active areas A120, the active areas A210, and the active areas A220 are each an area configured to convert visible light emitted by a scintillator into an electrical signal. The active areas are formed by doping a region in the vicinity of the surface of the silicon wafer with boron or phosphorus.

When being viewed from the direction perpendicular to the detection surface of the X-ray detector, each of the active areas A110, the active areas A120, the active areas A210, and the active areas A220 is in the shape of a rectangle of which one pair of opposing sides extends parallel to the X-direction and of which the other pair of opposing sides extends parallel to the Y-direction. Further, each of the active areas A110 is formed in a position apart from the end parts, in terms of the X-direction and the Y-direction, of the photodiode array 920. Each of the active areas A120 is formed in a position apart from the end parts, in terms of the Y-direction, of the photodiode array 920. Each of the active areas A210 is formed in a position apart from the end parts, in terms of the X-direction, of the photodiode array 920. The active areas are positioned in this manner because there are active-area formation prohibited areas in the end parts, in terms of the X-direction and the Y-direction, of each of the photodiode arrays 920, for the reasons stated below.

When the silicon wafer having the active areas A110, the active areas A120, the active areas A210, and the active areas A220 formed on the surface thereof is cut out so as to manufacture each of the photodiode arrays 920, very small cracks may occur in end parts of the silicon wafer. Also, to prevent the cracks from developing toward the inside of the silicon wafer, a groove is formed on the surface of the silicon wafer before the silicon wafer is cut out. Further, in a region of each of the photodiodes P110 other than the active area A110, a wiring connected to the active area A110 is installed, for example. Also, in a region of each of the photodiodes P120 other than the active area A120 and in a region of each of the photodiodes P210 other than the active area A210, wirings and the like are installed.

Further, in the conventional X-ray detector, to uniformly detect the X-rays radiated by the X-ray tube 6, the intervals between any two of the active areas positioned adjacent to each other in the X-direction and the Y-direction are equal to one another. The expression "intervals between any two of the active areas" denotes the intervals recognized when the conventional X-ray CT apparatus reconstructs the projection data.

Accordingly, the width of each of the active areas A110 in the X-direction is smaller than the width of each of the active areas A220 in the X-direction. The width of each of the active areas A110 in the Y-direction is smaller than the width of each of the active areas A220 in the Y-direction. Further, the width of each of the active areas A120 in the Y-direction smaller than the width of each of the active areas A220 in the Y-direction. Also, the width of each of the active areas A210 in the X-direction is smaller than the width of each of the active areas A220 in the X-direction.

As a result, in some situations, the detection efficiency levels or the SN ratios of the photodiodes P110, the photodiodes P120, and the photodiodes P210 may be lower than the detection efficiency levels or the SN ratios of the photodiodes P220. Also, an artifact may occur due to the lower detection efficiency level and/or SN ratios.

As illustrated in FIGS. 4 and 5, a scintillator array 910 is disposed on the +Z direction side of the photodiode array 920. The scintillator array 910 includes a plurality of scintillators of which the lateral faces extending parallel to the Y-Z plane and the lateral faces extending parallel to the Z-X plane are covered by a reflecting member. For example, the scintillator array 910 includes scintillators S120, scintillators S210, and scintillators S220.

The widths in the X-direction are equal between the scintillators and the photodiodes overlapping one another in the Z-direction. The widths in the Y-direction are equal between the scintillators and the photodiodes overlapping one another in the Z-direction. For example, the width of each of the scintillators S120 in the X-direction is equal to the width of each of the photodiodes P120 in the X-direction. As illustrated in FIG. 5, the width of each of the scintillators S120 in the Y-direction is equal to the width of each of the photodiodes P120 in the Y-direction. As illustrated in FIG. 4, the width of each of the scintillators S210 in the X-direction is equal to the width of each of the photodiodes P210 in the X-direction. The width of each of the scintillators S210 in the Y-direction is equal to the width of each of the photodiodes P210 in the Y-direction. As illustrated in FIGS. 4 and 5, the width of each of the scintillators S220 in the X-direction is equal to the width of each of the photodiode P220 in the X-direction. As illustrated in FIGS. 4 and 5, the width of each of the scintillators S220 in the Y-direction is equal to the width of each of the photodiodes P220 in the Y-direction.

Further, as illustrated in FIGS. 4 and 5, each of the scintillators included in the scintillator array 910 covers only one active area in the X-direction and the Y-direction. For example, as illustrated in FIGS. 4 and 5, each of the scintillators S220 covers only one active area A220 in the X-direction and the Y-direction. Similarly, each of the scintillators S120 covers only one active area A120 in the X-direction and the Y-direction. Further, each of the scintillators S210 covers only one active area A210 in the X-direction and the Y-direction. Accordingly, the visible light emitted by each of the scintillators is converted into an electrical signal only by one active area.

Next, the X-ray detector 9a according to the first embodiment will be explained, with reference to FIGS. 6, 7, and 8. In the X-ray detector 9a, the widths of the active areas are equal to one another, in at least one selected from between the first direction and the second direction.

Figure 6:
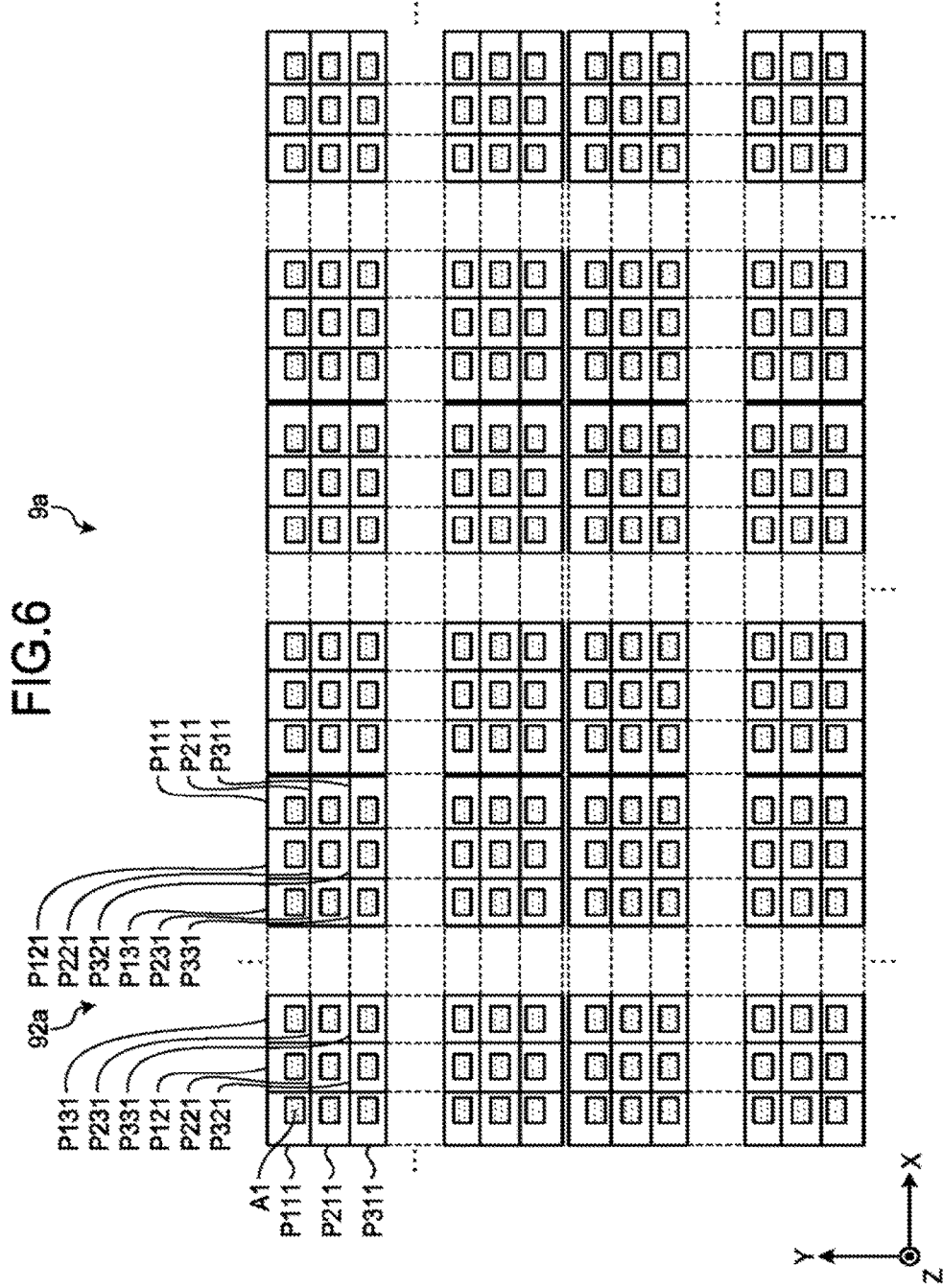
FIG. 6 is a drawing of an example of positional arrangements photodiodes and active areas included in an X-ray detector according to the first embodiment.

FIG. 6 is a drawing of an example of positional arrangements of photodiodes and active areas included in an X-ray detector according to the first embodiment. FIG. 7 is a cross-sectional view of one of the photodiode arrays illustrated in FIG. 6 and a scintillator array positioned on the +Z direction side of the photodiode array, being cross-sectioned by a plane that passes through active areas and is positioned parallel to the Z-X plane and being viewed from the −Y direction. FIG. 8 is a cross-sectional view of the one of the photodiode arrays illustrated in FIG. 6 and the scintillator array positioned on the +Z direction side of the photodiode array, being cross-sectioned by a plane that passes through active areas and is positioned parallel to the Y-Z plane and being viewed from the +X direction.

As illustrated in FIG. 6, in the X-ray detector 9a according to the first embodiment, the photodiode arrays 92a are arranged at certain intervals in the X-direction and the Y-direction.

Each of the photodiode arrays 92a includes a plurality of photodiodes. For example, as illustrated in FIG. 6, each of the photodiode arrays 92a includes photodiodes P111, photodiodes P121, photodiodes P131, photodiodes P211, photodiodes P221, photodiodes P231, photodiodes P311, photodiodes P321, and photodiodes P331. When being viewed from the direction perpendicular to the detection surface of the X-ray detector 9a, each of these photodiodes is in the shape of a rectangle of which one pair of opposing sides extends parallel to the X-direction and of which the other pair of opposing sides extends parallel to the Y-direction.

For example, a photodiode P111 is arranged in the first row in the first column (hereinafter, "row 1, column 1") of the photodiode array 92a. A photodiode P121 is arranged in row 1, column 2 of the photodiode array 92a. A photodiode P131 is arranged in row 1, column 3 of the photodiode array 92a. A photodiode P211 is arranged in row 2, column 1 of the photodiode array 92a. A photodiode P221 is arranged in row 2, column 2 of the photodiode array 92a. A photodiode P231 is arranged in row 2, column 3 of the photodiode array 92a. A photodiode P311 is arranged in row 3, column 1 of the photodiode array 92a. A photodiode P321 is arranged in row 3, column 2 of the photodiode array 92a. A photodiode P331 is arranged in row 3, column 3 of the photodiode array 92a. In the present example, the "rows" refer to the arrays of photodiodes in the X-direction, whereas the "columns" refer to the arrays of photodiodes in the Y-direction. Further, the photodiodes included in the photodiode arrays 92a correspond to the pixels of the projection data described above.

The width in the X-direction of each of the photodiodes decreases in the X-direction from the end parts of the photodiode array 2 toward the center thereof. For example, as illustrated in FIG. 6, the width of each of the photodiodes P121 in the X-direction is smaller than the width of each of the photodiodes P111 in the X-direction and is larger than the width of each of the photodiodes P131 in the X-direction. Similarly, the width of each of the photodiodes P221 in the X-direction is smaller than the width of each of the photodiodes P211 in the X-direction and is larger than the width of each of the photodiodes P231 in the X-direction. Further, the width of each of the photodiodes P321 in the X-direction is smaller than the width of each of the photodiodes P311 in the X-direction and is larger than the width of each of the photodiodes P331 in the X-direction.

Further, as illustrated in FIG. 6, the widths of the photodiodes P111, the photodiodes P121, the photodiodes P131, and so on in the Y-direction are equal to one another. Similarly, as illustrated in FIG. 6, the widths of the photodiodes P211, the photodiodes P221, the photodiodes P231, and so on in the Y-direction are equal to one another. Also, as illustrated in FIG. 6, the widths of the photodiodes P311, the photodiodes P321, the photodiodes P331, and so on in the Y-direction are equal to one another.

The width in the Y-direction of each of these photodiodes decreases in the Y-direction from the end parts of the photodiode array 92a toward the center thereof. For example, as illustrated in FIG. 6, the width of each of the photodiodes P211 in the Y-direction is smaller than the width of each of the photodiodes P111 in the Y-direction and is larger than the width of each of the photodiodes P311 in the Y-direction. Similarly, the width of each of the photodiodes P221 in the Y-direction is smaller than the width of each of the photodiodes P121 in the Y-direction and is larger than the width of each of the photodiodes P321 in the Y-direction. Also, the width of each of the photodiodes P231 in the Y-direction is smaller than the width of each of the photodiodes P131 in the Y-direction and is larger than the width of each of the photodiodes P331 in the Y-direction.

Further, as illustrated in FIG. 6, the widths of the photodiodes P111, the photodiodes P211, the photodiodes P311, and so on in the X-direction are equal to one another. Similarly, as illustrated in FIG. 6, the widths of the photodiodes P121, the photodiodes P221, the photodiodes P321, and so on in the X-direction are equal to one another. Further, as illustrated in FIG. 6, the widths of the photodiodes P131, the photodiodes P231, the photodiodes P331, and so on in the X-direction are equal to one another.

Each of the photodiodes included in each of the photodiode arrays 92a has an active area A1. For example, as illustrated in FIG. 6, each of the photodiodes P111, the photodiodes P121, the photodiodes P131, the photodiodes P211, the photodiodes P221, the photodiodes P231, the photodiodes P311, the photodiodes P321, and the photodiodes P331 has the active area A1. The active areas A1 are each an area configured to convert visible light emitted by a scintillator into an electrical signal. The active areas A1 are formed by doping a region in the vicinity of the surface of the silicon wafer with boron or phosphorus.

When being viewed from the direction perpendicular to the detection surface of the X-ray detector 9a, each of the active areas A1 is in the shape of a rectangle of which one pair of opposing ides extends parallel to the X-direction and of which the other pair of opposing sides extends parallel to the Y-direction. Accordingly, the X-ray detector 9a is configured in such a manner that the difference in the width between any two of the active areas positioned adjacent to each other in the first direction and the difference in the width between any two of the active areas positioned adjacent to each other in the second direction are zero. Further, the X-ray detector 9a is configured in such a manner that the widths of the active areas in the first direction are equal to one another, and the widths of the active areas in the second direction are equal to one another.

Further, each of the active areas A1 is formed in a position apart from the end parts, in terms of the X-direction and the Y-direction, of the photodiode array 92a. The active areas A1 are positioned in this manner because there are active-area formation prohibited areas in the end parts, in terms of the X-direction and the Y-direction, of each of the photodiode arrays 92a, for the reasons stated below.

When the silicon wafer having the active areas A1 formed on the surface thereof is cut out so as to manufacture each of the photodiode arrays 92a, very small cracks may occur in end parts of the silicon wafer. Also, to prevent the cracks from developing toward the inside of the silicon wafer, a groove is formed on the surface of the silicon wafer before the silicon wafer is cut out. Further, in a region of each of the photodiodes other than the active area A1, a wiring connected to the active area A1 is installed, for example.

The interval in the X-direction between each pair of active areas A1 increases in the X-direction from the end parts of the photodiode array 92a toward the center thereof. In this situation, the expression "the interval in the X-direction between each pair of active areas A1" denotes the distance between the centers of each pair of adjacently-positioned active areas A1 in the X-direction. Further, as explained above, the width in the X-direction of each of the photodiodes included in each of the photodiode arrays 92a decreases in the X-direction from the end parts of the photodiode array 92a toward the center thereof. Accordingly, as illustrated in FIG. 6, it is possible to configure the X-ray detector 9a in such a manner that the widths in the X-direction of all the active areas A1 included in the photodiode arrays 92a are equal to one another.

Further, as illustrated in FIG. 6, the center of each of the photodiodes P131 in the X-direction is the same as the center of the corresponding one of the active areas A1 in the X-direction. Similarly, the center of each of the photodiodes P231 in the X-direction is the same as the center of the corresponding one of the active areas A1 in the X-direction. Also, the center of each of the photodiodes P331 in the X-direction is the same as the center of the corresponding one of the active areas A1 in the X-direction.

The interval in the Y-direction between each pair of active areas A1 increases in the Y-direction from the end parts of the photodiode array 92a toward the center thereof. In this situation, the expression "the interval in the Y-direction between each pair of active areas A1" denotes the distance between the centers of each pair of adjacently-positioned active areas A1 in the Y-direction. Further, as explained above, the width in the Y-direction of each of the photodiodes included in each of the photodiode arrays 92a decreases in the Y-direction from the end parts of the photodiode array 92a toward the center thereof. Accordingly, as illustrated in FIG. 6, it is possible to configure the X-ray detector 9a in such a manner that the widths in the Y-direction of all the active areas A1 included in the photodiode arrays 92a are equal to one another.

Further, as illustrated in FIG. 6, the center of each of the photodiodes P311 in the Y-direction is the same as the center of the corresponding one of the active areas A1 in the Y-direction. Similarly, the center of each of the photodiodes P321 in the Y-direction is the same as the center of the corresponding one of the active areas A1 in the Y-direction. Also, the center each of the photodiodes P331 in the Y-direction is the same as the center of the corresponding one of the active areas A1 in the Y-direction.

Figure 7:
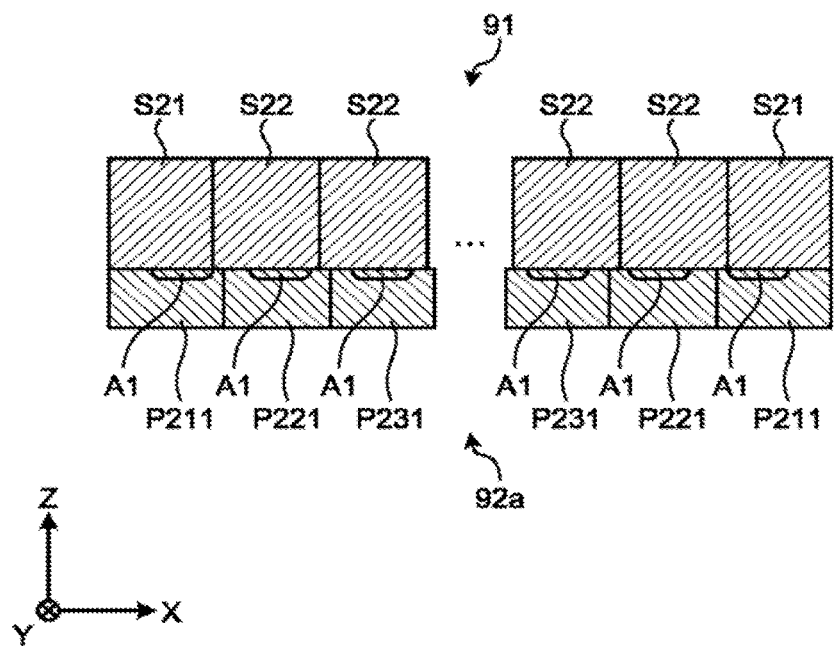
FIG. 7 is a cross-sectional view of one of the photodiode arrays illustrated in FIG. 6 and a scintillator array positioned on the +Z direction side of the photodiode array, being cross-sectioned by a plane that passes through active areas and is positioned parallel to the Z-X plane and being viewed from the −Y direction.
Figure 8:
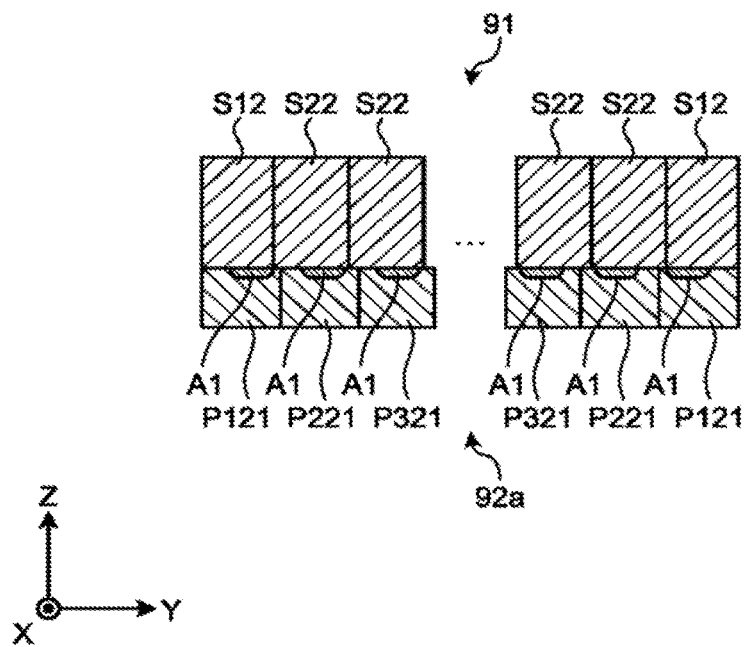
FIG. 8 is a cross-sectional view of the one of the photodiode arrays illustrated in FIG. 6 and the scintillator array positioned on the +Z direction side of the photodiode array, being cross-sectioned by a plane that passes through active areas and is positioned parallel to the Y-Z plane and being viewed from the +X direction.

Further, as illustrated in FIGS. 7 and 8, a scintillator array 91 is disposed on the +Z direction side of the photodiode array 92a. The scintillator array 91 includes a plurality of scintillators of which the lateral faces extending parallel to the Y-Z plane and the lateral faces extending parallel to the Z-X plane are covered by a reflecting member.

Each of the scintillator arrays 91 includes scintillators each having a smaller width in the X-direction and scintillators each having a larger width in the X-direction. For example, as illustrated in FIG. 7, each of the scintillator arrays 91 includes scintillators S21 each having a smaller width in the X-direction and scintillators S22 each having a larger width in the X-direction. The width of each of the scintillators S21 in the X-direction is smaller than the width of each of the scintillators S22 in the X-direction. The scintillators S21 are disposed in the end part in terms of the +X direction side and in the end part in terms of the −X direction side of each of the scintillator arrays 91. The scintillators S22 are disposed between two scintillators S21.

As illustrated in FIG. 7, the intervals between the scintillators in the X-direction are different from the intervals between the photodiodes in the X-direction. In this situation, the expression "the intervals between the scintillators in the X-direction" denotes the intervals recognized when the X-ray CT apparatus 1 reconstructs the projection data. Further, the expression "the intervals between the photodiodes in the X-direction" denotes the distances between the centers of the pairs of adjacently-positioned photodiodes in the X-direction. Further, a illustrated in FIG. 7, the sum of the widths in the X-direction of the two scintillators S21 and the plurality of scintillators S22 disposed therebetween is equal to the sum of the widths in the X-direction of the photodiode P211, the photodiode P221, the photodiode P231, . . . , the photodiode P231, the photodiode P221, and the photodiode P211.

Figure 9:
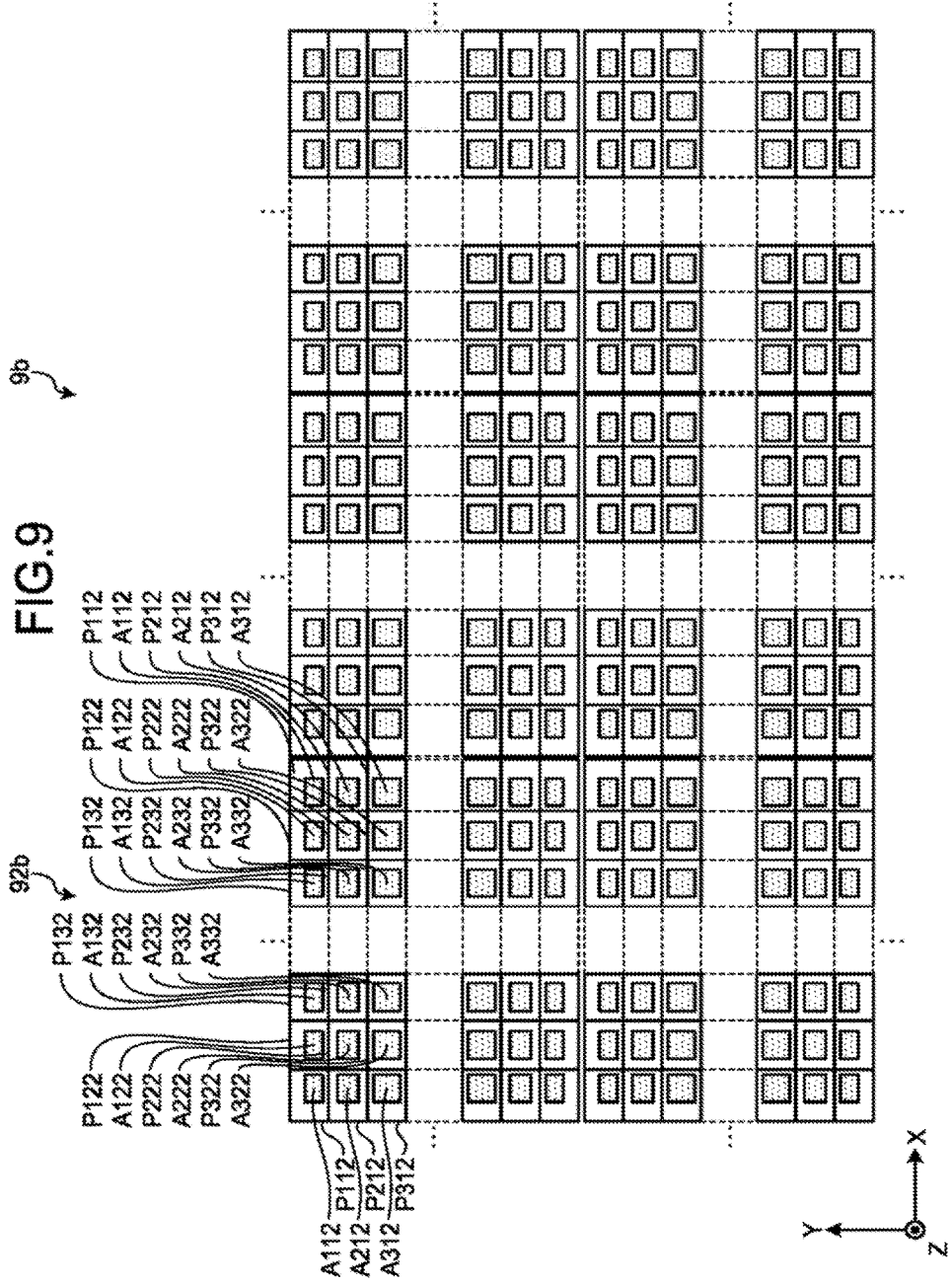
FIG. 9 is a drawing of an example of positional arrangements of photodiodes and active areas included in an X-ray detector according to a second embodiment.

Each of the scintillator arrays 91 includes scintillators each having a smaller width in the Y-direction and scintillators each having a larger width in the Y-direction. For example, as illustrated in FIG. 9, each of the scintillator arrays 91 includes scintillators S12 each having a smaller width in the Y-direction and scintillators S22 each having a larger width in the Y-direction. The width of each of the scintillators S12 in the Y-direction is smaller than the width of each of the scintillators S22 in the Y-direction. The scintillators S12 are disposed in the end part in terms of the +Y direction side and in the end part in terms of the −Y direction side of each of the scintillator arrays 91. The scintillators S22 are disposed between two scintillators S12.

As illustrated in FIG. 9, the intervals between the scintillators in the Y-direction are different from the intervals between the photodiodes in the Y-direction. In this situation, the expression "the intervals between the scintillators in the Y-direction" denotes the intervals recognised when the X-ray CT apparatus 1 reconstructs the projection data. Further, the expression "the intervals between the photodiode in the Y-direction" denotes the distances between the centers of the pairs of adjacently-positioned photodiodes in the Y-direction. Further, as illustrated in FIG. 8, the sum of the widths in the Y-direction of the two scintillators S12 and the plurality of scintillators S22 disposed therebetween is equal to the sum of the widths in the Y-direction of the photodiode P121, the photodiode P221, the photodiode P321, . . . , the photodiode P321, the photodiode P221, and the photodiode P121.

Further, as illustrated in FIGS. 7 and 8, each of the scintillators included in each of the scintillator arrays 91 covers only one active area A1 in the X-direction and the Y-direction. For example, as illustrated in FIGS. 7 and 8, each of the scintillators S22 covers only one active area A1 in the X-direction and the Y-direction. Similarly, each of the scintillators S12 covers only one active area A1 in the X-direction and the Y-direction. Further, each of the scintillators S21 covers only one active area A1 in the X-direction and the Y-direction. Accordingly, the visible light emitted by each of the scintillators is converted into an electrical signal only by one active area A1.

As explained above, the X-ray detector 9a according to the first embodiment is configured in such a manner that the difference in the width between any two of the active areas positioned adjacent to each other in the first direction and the difference in the width between any two of the active areas positioned adjacent to each other in the second direction are zero and that the intervals between the pairs of adjacently-positioned active areas exhibit multiple values. Further, the X-ray detector 9a according to the first embodiment is configured in such a manner that the widths of the active areas in the first direction are equal to one another and that the widths of the active areas in the second direction are equal to one another. Accordingly, the detection efficiency levels and the SN ratios are equal among all the photodiodes included in the X-ray detector 9a according to the first embodiment. Consequently, the X-ray detector 9a according to the first embodiment is able to suppress the occurrence of artifacts that may be caused by the detection efficiency levels or the SN ratios being different among the photodiodes.

Second Embodiment

An X-ray detector 9b according to a second embodiment will be explained. Further, some of the constituent elements that are the same as those in the first embodiment will be referred to by using the same reference characters those used in the description of the first embodiment. Detailed explanations of some of the configurations that are duplicates of those in the first embodiment will be omitted.

The X-ray detector 9b according to the second embodiment will be explained, with reference to FIGS. 9, 10, and 11. In the X-ray detector 9b, the width of each of the active areas increases from the end parts of the photodiode array toward the center thereof, in at least one selected from between the first direction and the second direction.

FIG. 9 is a drawing of an example of positional arrangements of photodiodes and active areas included in an X-ray detector according to the second embodiment. FIG. 10 is a cross-sectional view of one of the photodiode arrays illustrated in FIG. 9 and a scintillator array positioned on the +Z direction side of the photodiode array, being cross-sectioned by a plane that passes through active areas and is positioned parallel to the Z-X plane and being viewed from the −Y direction. FIG. 11 is a cross-sectional view of the one of the photodiode arrays illustrated in FIG. 9 and the scintillator array positioned on the +Z direction side of the photodiode array, being cross-sectioned by a plane that passes through active areas and is positioned parallel to the Y-Z plane and being viewed from the +X direction.

As illustrated in FIG. 9, in the X-ray detector 9b according to the second embodiment, photodiode arrays 92b are arranged at certain intervals in the X-direction and the Y-direction.

Each of the photodiode arrays 92b includes a plurality of photodiodes. For example, as illustrated in FIG. 9, each of the photodiode arrays 92b includes photodiodes P112, photodiodes P122, photodiodes P132, photodiodes P212, photodiodes P222, photodiodes P232, photodiodes P312, photodiodes P322, and photodiodes P332.

The width in the X-direction of each of the photodiodes included in each of the photodiode arrays 92b decreases in the X-direction from the end parts of the photodiode array 92b toward the center thereof. For example, as illustrated in FIG. 9, the width of each of the photodiodes P122 in the X-direction is smaller than the width of each of the photodiodes P112 in the X-direction and is larger than the width of each of the photodiodes P132 in the X-direction. Similarly, the width of each of the photodiodes P222 in the X-direction is smaller than the width of each of the photodiodes P212 in the X-direction and is larger than the width of each of the photodiodes P232 in the X-direction. Further, the width of each of the photodiodes P322 in the X-direction is smaller than the width of each of the photodiodes P312 in the X-direction and is larger than the width of each of the photodiodes P332 in the X-direction.

Further, as illustrated in FIG. 9, the widths of the photodiodes P112, the photodiodes P122, the photodiodes P132, and so on in the Y-direction are equal to one another. Similarly, as illustrated in FIG. 9, the widths of the photodiodes P212, the photodiodes P222, the photodiodes P232, and so on in the Y-direction are equal to one another. Also, as illustrated in FIG. 9, the widths of the photodiodes P312, the photodiodes P322, the photodiodes P332, and so on in the Y-direction are equal to one another.

The width in the Y-direction of each of the photodiodes included in each of the photodiode arrays 92b decreases in the Y-direction from the end parts of the photodiode array 92b toward the center thereof. For example, as illustrated in FIG. 9, the width of each of the photodiodes P212 in the Y-direction is smaller than the width of each of the photodiodes P112 in the Y-direction and is larger than the width of each of the photodiodes P312 in the Y-direction. Similarly, the width of each of the photodiodes P222 in the Y-direction is smaller than the width of each of the photodiodes P122 in the Y-direction and is larger than the width of each of the photodiodes P322 in the Y-direction. Also, the width of each of the photodiodes P232 in the Y-direction is smaller than the width of each of the photodiodes P132 in the Y-direction and is larger than the width of each of the photodiodes P332 in the Y-direction.

Further, as illustrated in FIG. 9, the widths of the photodiodes P112, the photodiodes P212, the photodiodes P312, and so on in the X-direction are equal to one another. Similarly, as illustrated in FIG. 9, the widths of the photodiodes P122, the photodiodes P222, the photodiodes P322, and so on in the X-direction are equal to one another. Also, as illustrated in FIG. 9, the widths of the photodiodes P132, the photodiodes P232, the photodiodes P332, and so or in the X-direction are equal to one another.

Each of the photodiodes included in each of the photodiode arrays 92b has an active area. For example, as illustrated in FIG. 9, each of the photodiodes P112 has an active area A112. Each of the photodiodes P122 has an active area A122. Each of the photodiodes P132 has an active area A132. Each of the photodiodes P212 has an active area A212. Each of the photodiodes P222 has an active area A222. Each of the photodiodes P232 has an active area A232. Each of the photodiodes P312 has an active area A312. Each of the photodiodes P322 has an active area A322. Each of the photodiodes P332 has an active area A332.

Each of the active areas A112 is formed in a position apart from the end parts, in terms of the X-direction and the Y-direction, of the photodiode array 92b. Each of the active areas A212, the active areas A312, and the like is formed in a position apart from the end parts, in terms of the X-direction, of the photodiode array 92b. Each of the active area A122, the active areas A132, and the like is formed in a position apart from the end parts, in terms of the Y-direction, of the photodiode array 92b. The active areas are positioned in this manner because, similarly to the first embodiment, there are active-area formation prohibited areas in the end parts, in terms of the X-direction and the Y-direction, of each of the photodiode arrays 92b.

The width in the X-direction of each of the active areas included in each of the photodiode arrays 92b increases in the X-direction from the end parts of the photodiode array 92b toward the center thereof. For example, as illustrated in FIG. 9, the width of each of the active areas A122 in the X-direction is larger than the width of each of the active areas A112 in the X-direction and is smaller than the width of each of the active areas A132 in the X-direction. Similarly, the width of each of the active areas A222 in the X-direction is larger than the width of each of the active areas A212 in the X-direction and is smaller than the width of each of the active areas A232 in the X-direction. Also, the width of each of the active areas A322 in the X-direction is larger than the width of each of the active areas A312 in the X-direction and is smaller than the width of each of the active areas A332 in the X-direction. It should be noted, however, that the difference in the width between any two of the active areas positioned adjacent to each other in the X-direction is within a predetermined range.

The width in the X-direction of each of the active areas included in each of the photodiode arrays 92b may keep increasing in the X-direction from the end parts of the photodiode array 92b toward the center thereof. Alternatively, the width in the X-direction of each of the active areas included in each of the photodiode arrays 92b may arrive at a maximum value before reaching the center of the photodiode array 92b from an end part of the photodiode array 92b in the X-direction and may thereafter decrease. In another example, the width in the X-direction of each of the active areas included in each of the photodiode arrays 92b may arrive at a maximum value before reaching the center of the photodiode array 92b from an end part of the photodiode array 92b in the X-direction, so that the widths of a predetermined number of photodiodes thereafter each exhibit the maximum value, before the width starts decreasing thereafter.

Further, as illustrated in FIG. 9, the widths of the active areas A112, the active areas A122, the active areas A132, and so on in the Y-direction are equal to one another. Similarly, as illustrated in FIG. 9, the widths of the active areas A212, the active areas A222, the active areas A232, and so on in the Y-direction are equal to one another. Also, as illustrated in FIG. 9, the widths of the active areas A312, the active areas A322, the active areas A332, and so on in the Y-direction are equal to one another.

The width in the Y-direction of each of the active areas included in each of the photodiode arrays 92b increases in the Y-direction from the end parts of the photodiode array 92b toward the center thereof. For example, as illustrated in FIG. 9, the width of each of the active areas A212 in the Y-direction is larger than the width of each of the active areas A112 in the Y-direction and is smaller than the width of each of the active areas A312 in the Y-direction. Similarly, the width of each of the active areas A222 in the Y-direction is larger than the width of each of the active areas A122 in the Y-direction and is smaller than the width of each of the active areas A322 in the Y-direction. Also, the width of each of the active areas A232 in the Y-direction is larger than the width of each of the active areas A132 in the Y-direction and is smaller than the width of each of the active areas A332 in the Y-direction. It should be noted, however, that the difference in the width between any two of the active areas positioned adjacent to each other in the Y-direction is within a predetermined range.

The width in the Y-direction of each of the active areas included in each of the photodiode arrays 92b may keep increasing in the Y-direction from the end parts of the photodiode array 92b toward the center thereof. Alternatively, the width in the Y-direction of each of the active areas included in each of the photodiode arrays 92b may arrive at a maximum value before reaching the center of the photodiode array 92b from an end part of the photodiode array 92b in the Y-direction and may thereafter decrease. In another example, the width in the Y-direction of each of the active areas included in each of the photodiode arrays 92b may arrive at a maximum value before reaching the center of the photodiode array 92b from an end part of the photodiode array 92b in the Y-direction, so that the widths of a predetermined number of photodiodes thereafter each exhibit the maximum value, before the width starts decreasing thereafter.

Further, as illustrated in FIG. 9, the widths of the active areas A112, the active areas A212, the active areas A312, and so on in the X-direction are equal to one another. Similarly, as illustrated in FIG. 9, the widths of the active areas A122, the active areas A222, the active areas A322, and so on in the X-direction are equal to one another. Also, as illustrated in FIG. 9, the widths of the active areas A132, the active areas A232, the active areas A332, and so on in the X-direction are equal to one another.

The interval in the X-direction between each pair of active areas included in each of the photodiode arrays 92b increases in the X-direction from the end parts of the photodiode array 92b toward the center thereof. In this situation, the expression "the interval in the X-direction between each pair of active areas" denotes the distance between the centers of each pair of adjacently-positioned active areas in the X-direction. For example, as illustrated in FIG. 9, the interval in the X-direction between the active area A122 and the active area A132 is larger than the interval in the X-direction between the active area A112 and the active area A122. Similarly, the interval in the X-direction between the active area A222 and the active area A232 is larger than the interval in the X-direction between the active area A212 and the active area A222. Also, the interval in the X-direction between the active area A322 and the active area A332 is larger than the interval in the X-direction between the active area A312 and the active area A322. In other words, the intervals between the pairs of active areas positioned adjacent to each other in the X-direction exhibit multiple values.

Further, as explained above, the width in the X-direction of each of the photodiodes included in each of the photodiode arrays 92b decreases in the X-direction from the end parts of the photodiode array 92b toward the center thereof. Accordingly, as explained above, it is possible to configure the X-ray detector 9b in such a manner that, as illustrated in FIG. 9, the width in the X-direction of each of active areas included in each of the photodiode arrays 92b increases from the end parts of the photodiode array 92b toward the center thereof.

Further, as illustrated in FIG. 9, the center of each of the photodiodes P132 in the X-direction is the same as the center of the corresponding one of the active areas A132 in the X-direction. Similarly, the center of each of the photodiodes P232 in the X-direction is the same as the center of the corresponding one of the active areas A232 in the X-direction. Also, the center of each of the photodiodes P332 in the X-direction is the same as the center of the corresponding one of the active areas A332 in the X-direction.

The interval in the Y-direction between each pair of active areas included in each of the photodiode arrays 92b increases in the Y-direction from the end parts of the photodiode array 92b toward the center thereof. In this situation, the expression "the interval in the Y-direction between each pair of active areas" denotes the distance between the centers of each pair of adjacently-positioned active areas in the Y-direction. For example, as illustrated in FIG. 9, the interval in the Y-direction between the active area A212 and the active area A312 is larger than the interval in the Y-direction between the active area A112 and the active area A212. Similarly, the interval in the Y-direction between the active area A222 and the active area A322 is larger than the interval in the Y-direction between the active area A122 and the active area A222. Also, the interval in the Y-direction between the active area A232 and the active area A332 is larger than the interval in the Y-direction between the active area A132 and the active area A232. In other words, the intervals between the pairs of active areas positioned adjacent to each other in the Y-direction exhibit multiple values.

Further, as explained above, the width in the Y-direction of each of the photodiodes included in each of the photodiode arrays 92b decreases in the Y-direction from the end parts of the photodiode array 92b toward the center thereof. Accordingly, as explained above, it is possible to configure the X-ray detector 9b in such a manner that, as illustrated in FIG. 9, the width in the Y-direction of each of the active areas included in each of the photodiode arrays 92b increases from the end parts of the photodiode array 92b toward the center thereof.

Further, as illustrated in FIG. 9, the center of each of the photodiodes P312 in the Y-direction is the same as the center of the corresponding one of the active areas A312 in the Y-direction. Similarly, the center of each of the photodiodes P322 in the Y-direction is the same as the center of the corresponding one of the active areas A322 in the Y-direction. Also, the center of each of the photodiodes P332 in the Y-direction is the same as the center of the corresponding one of the active areas A332 in the Y-direction.

Figure 10:
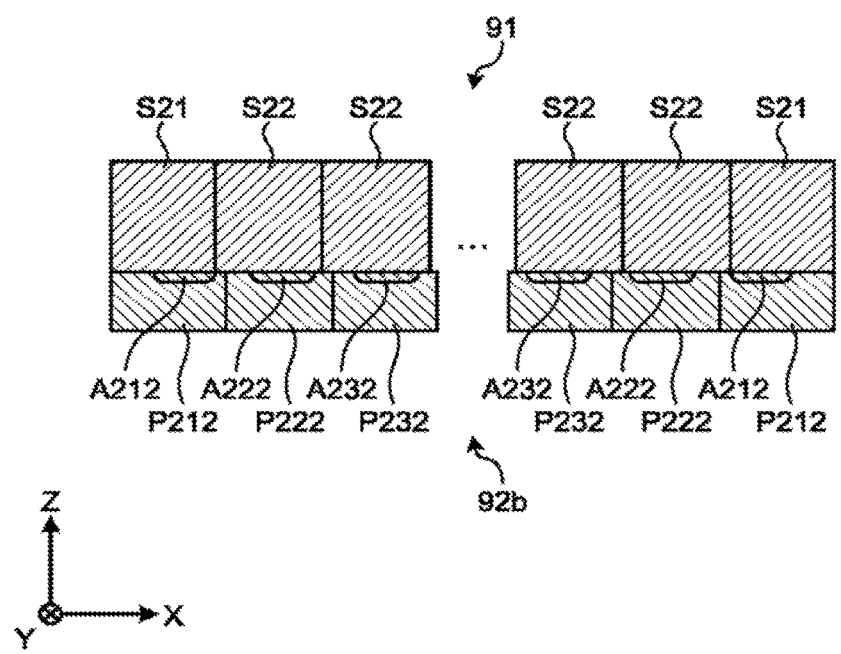
FIG. 10 is a cross-sectional view of one of the photodiode arrays illustrated in FIG. 9 and a scintillator array positioned on the +Z direction side of the photodiode array, being cross-sectioned by a plane that passes through active areas and is positioned parallel to the Z-X plane and being viewed from the −Y direction.
Figure 11:
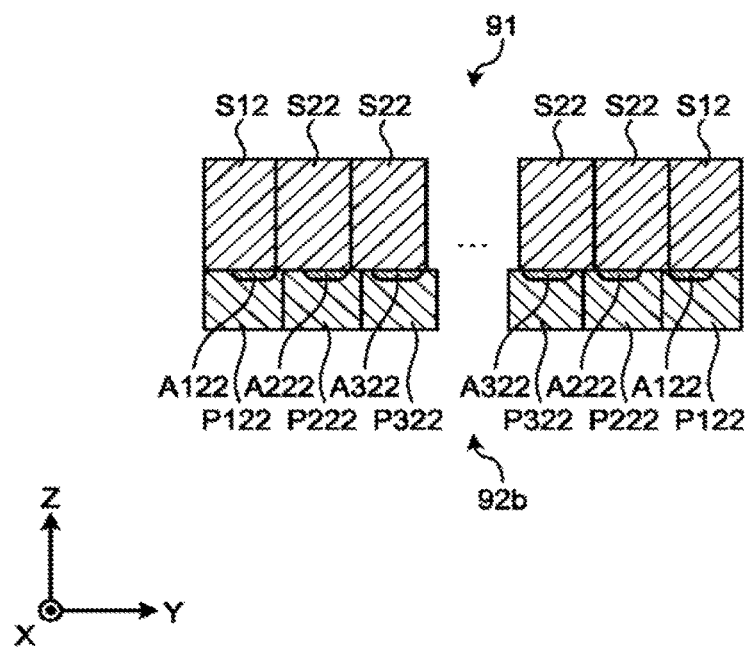
FIG. 11 is a cross-sectional view of the one of the photodiode arrays illustrated in FIG. 9 and the scintillator array positioned on the +Z direction side of the photodiode array, being cross-sectioned by a plane that passes through active areas and is positioned parallel to the Y-Z plane and being viewed from the +X direction.

Further, as illustrated in FIGS. 10 and 11, the scintillator array 91 is disposed on the +Z direction side of the photodiode array 92b.

As illustrated in FIG. 10, the intervals between the scintillators in the X-direction are different from the intervals between the photodiodes in the X-direction. In this situation, the expression "the intervals between the scintillators in the X-direction" denotes the intervals recognized when the X-ray CT apparatus 1 reconstructs the projection data. Further, in this situation, the expression "the intervals between the photodiodes in the X-direction" denotes the distances between the centers of the pairs of adjacently-positioned photodiodes in the X-direction. Further, as illustrated in FIG. 10, the sum of the widths in the X-direction of the two scintillators S21 and the plurality of scintillators S22 disposed therebetween is equal to the sum of the widths in the X-direction of the photodiode P212, the photodiode P222, the photodiode P232, . . . , the photodiode P232, the photodiode P222, and the photodiode P212.

As illustrated in FIG. 11, the intervals between the scintillators in the Y-direction are different from the intervals between the photodiodes in the Y-direction. In this situation, the expression "the intervals between the scintillators in the Y-direction" denotes the intervals recognized when the X-ray CT apparatus 1 reconstructs the projection data. Further, in this situation, the expression "the intervals between the photodiodes in the Y-direction" denotes the distances between the centers of the pairs of adjacently-positioned photodiodes in the Y-direction. Further, as illustrated in FIG. 11, the sum of the widths in the Y-direction of the two scintillators S12 and the plurality of scintillators S22 disposed therebetween is equal to the sum of the widths in the Y-direction of the photodiode P122, the photodiode P222, the photodiode P322, . . . , the photodiode P322, the photodiode P222, and the photodiode P122.

Further, as illustrated in FIGS. 10 and 11, each of the active areas included in each of the photodiode arrays 92b is covered by only one scintillator in the X-direction and the Y-direction. For example, as illustrated in FIGS. 10 and 11, each of the active areas A222 is covered by only one scintillator S22 in the X-direction and the Y-direction. Similarly, each of the active areas A232 is covered by only one scintillator S22 in the X-direction and the Y-direction. Also, each of the active areas A322 is covered by only one scintillator S22 in the X-direction and the Y-direction. Further, each of the active areas A212 is covered by only one scintillator S21 in the X-direction and the Y-direction. Furthermore, each of the active areas A122 is covered by only one scintillator S12 in the X-direction and the Y-direction.

As explained above, the X-ray detector 9b according to the second embodiment is configured in such a manner that the difference in the width between any two of the active areas positioned adjacent to each other in the first direction and the difference in the width between any two of the active areas positioned adjacent to each other in the second direction are within the predetermined range and that the intervals between the pairs of adjacently-positioned active areas exhibit multiple values. Further, the X-ray detector 9b according to the second embodiment is configured in such a manner that the width of each of the active areas increases in the first direction and the second direction from the end parts of the photodiode array toward the center thereof. Accordingly, the differences in the detection efficiency levels and the SN ratios among the photodiodes included in the X-ray detector 9b according to the second embodiment are kept small. Consequently, the X-ray detector 9b according to the second embodiment is able to suppress the occurrence of artifacts that may be caused by the detection efficiency levels or the SN ratios being different among the photodiodes.

Further, the X-ray detector 9b according to the second embodiment is configured in such a manner that, unlike the X-ray detector 9a according to the first embodiment, there is no need to arrange the widths of the active areas to be uniform in the first direction and the second direction. Accordingly, the X-ray detector 9b according to the second embodiment has fewer design constraints than the X-ray detector 9a according to the first embodiment. Consequently, for example, it is easier to enlarge the widths of the active areas in the X-direction and the Y-direction in the X-ray detector 9b according to the second embodiment than in the X-ray detector 9a according to the first embodiment. It is therefore possible to improve the detection efficiency levels and the SN ratios of the photodiodes.

Furthermore, in the X-ray detector 9b according to the second embodiment, it is easier to narrow the widths of the active areas positioned at the end parts of each of the photodiode arrays. Consequently, it is possible to more easily realize the X-ray detector 9b according to the second embodiment than the X-ray detector 9a according to the first embodiment.

Third Embodiment

An X-ray detector 9c according to a third embodiment will be explained. Further, some of the constituent elements that are the same as those in any of the embodiments described above will be referred to by using the same reference characters as those used in the description of the embodiment. Detailed explanations of some of the configurations that are duplicates of those in any of the embodiments described above will be omitted.

The X-ray detector 9c according to the third embodiment will be explained, with reference to FIGS. 12, 13, and 14. The X-ray detector 9c is configured in such a manner that, the width of each of the active areas decreases from the end parts of the photodiode array toward the center thereof, in at least one selected from between the first direction and the second direction.

Figure 12:
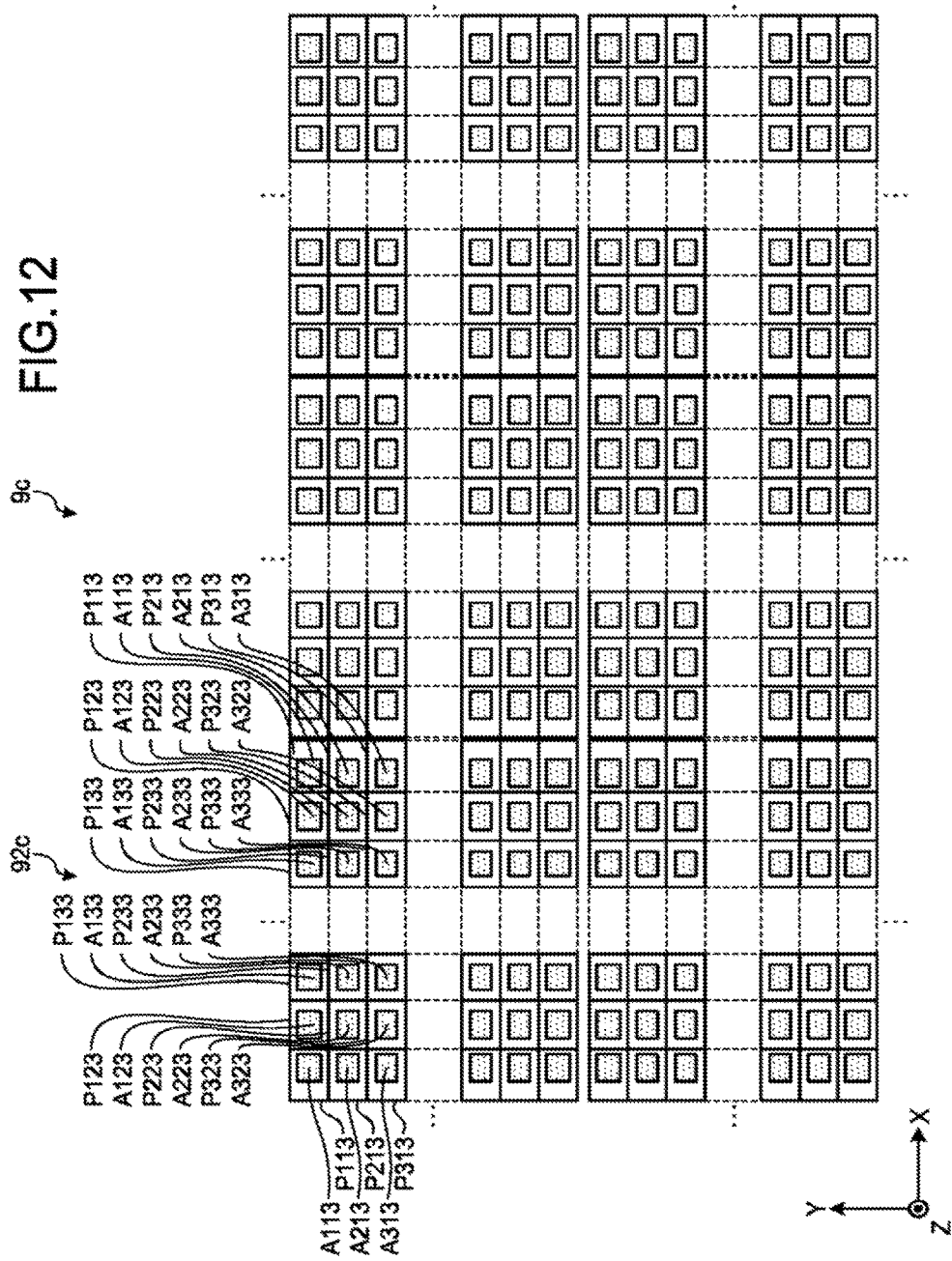
FIG. 12 is a drawing of an example of positional arrangements of photodiodes and active areas included in an X-ray detector according to a third embodiment.

FIG. 12 is a drawing of an example of positional arrangements of photodiodes and active areas included in an X-ray detector according to the third embodiment. FIG. 1 is a cross-sectional view of one of the photodiode arrays illustrated in FIG. 12 and a scintillator array positioned on the +Z direction side of the photodiode array, being cross-sectioned by a plane that passes through active areas and is positioned parallel to the Z-X plane and being viewed from the −Y direction. FIG. 14 is a cross-sectional view of the one of the photodiode arrays illustrated in FIG. 12 and the scintillator array positioned on the +Z direction side of the photodiode array, being cross-sectioned by a plane that passes through active areas and is positioned parallel to the Y-Z plane and being viewed from the +X direction.

As illustrated in FIG. 12, in the X-ray detector 9c according to the third embodiment, photodiode arrays 92c are arranged at certain intervals in the X-direction and the Y-direction.

Each of the photodiode arrays 92c includes a plurality of photodiodes. For example, as illustrated in FIG. 12, each of the photodiode arrays 92c includes photodiodes P113, photodiodes P123, photodiodes P133, photodiodes P213, photodiodes P223, photodiodes P233, photodiodes P313, photodiodes P323, and photodiodes P333.

The width in the X-direction of each of the photodiodes included in each of the photodiode arrays 92c decreases in the X-direction from the end parts of the photodiode array 92c toward the center thereof. For example, as illustrated in FIG. 12, the width of each of the photodiodes P123 in the X-direction is smaller than the width of each of the photodiodes P113 in the X-direction and is larger than the width of each of the photodiodes P133 in the X-direction. Similarly, the width of each of the photodiodes P223 in the X-direction is smaller than the width of each of the photodiodes P213 in the X-direction and is larger than the width of each of the photodiodes P233 in the X-direction. Further, the width of each of the photodiodes P323 in the X-direction is smaller than the width of each of the photodiodes P313 in the X-direction and is larger than the width of each of the photodiodes P333 in the X-direction.

Further, as illustrated in FIG. 12, the widths of the photodiodes P113, the photodiodes P123, the photodiodes P133, and so on in the Y-direction are equal to one another. Similarly, as illustrated in FIG. 12, the widths of the photodiodes P213, the photodiodes P223, the photodiodes P233, and so on in the Y-direction are equal to one another. Also, as illustrated in FIG. 12, the widths of the photodiodes P313, the photodiodes P323, the photodiodes P333, and so on in the Y-direction are equal to one another.

The width in the Y-direction of each of the photodiodes included in each of the photodiode arrays 92c decreases in the Y-direction from the end parts of the photodiode array 92c toward the center thereof. For example, as illustrated in FIG. 12, the width of each of the photodiodes P213 in the Y-direction is smaller than the width of each of the photodiodes P113 in the Y-direction and is larger than the width of each of the photodiodes P313 in the Y-direction. Similarly, the width of each of the photodiodes P223 in the Y-direction is smaller than the width of each of the photodiodes P123 in the Y-direction and is larger than the width of each of the photodiodes P323 in the Y-direction. Also, the width of each of the photodiodes P233 in the Y-direction is smaller than the width of each of the photodiodes P133 in the Y-direction and is larger than the width of each of the photodiodes P333 in the Y-direction.

Further, as illustrated in FIG. 12, the widths of the photodiodes P113, the photodiodes P213, the photodiodes P313, and so on in the X-direction are equal to one another. Similarly, as illustrated in FIG. 12, the widths of the photodiodes P123, the photodiodes P223, the photodiodes P323, and so on in the X-direction are equal to one another. Further, as illustrated in FIG. 12, the widths of the photodiodes P133, the photodiodes P233, the photodiodes P333, and so on in the X-direction are equal to one another.

Each of the photodiodes included in each of the photodiode arrays 92c has an active area. For example, as illustrated in FIG. 12, each of the photodiodes P113 has an active area A113. Each of the photodiodes P123 has an active area A123. Each of the photodiodes P133 has an active area A133. Each of the photodiodes P213 has an active area A213. Each of the photodiodes P223 has an active area A223. Each of the photodiodes P233 has an active area A233. Each of the photodiodes P313 has an active area A313. Each of the photodiodes P323 has an active area A323. Each of the photodiodes P333 has an active area A333.

Each of the active areas A113 is formed in a position apart from the end parts, in terms of the X-direction and the Y-direction, of the photodiode arrays 92c. Each of the active areas A213, the active areas A313, and the like is formed in a position apart from the end parts, in terms of the X-direction, of the photodiode array 92c. Each of the active areas A123, the active areas A133, and the like is formed in a position apart from the end parts, in terms of the Y-direction, of the photodiode array 92c. The active areas are positioned in this manner because, similarly to the first embodiment, there are active-area formation prohibited areas in the end parts, in terms of the X-direction and the Y-direction, of each of the photodiode arrays 92c.

The width in the X-direction of each of the active areas included in each of the photodiode arrays 92c decreases in the X-direction from the end parts of the photodiode array toward the center thereof. For example, as illustrated in FIG. 12, the width of each of the active areas A123 in the X-direction is smaller than the width of each of the active areas A113 in the X-direction and is larger than the width of each of the active areas A133 in the X-direction. Similarly, the width of each of the active areas A223 in the X-direction is smaller than the width of each of the active areas A213 in the X-direction and is larger than the width of each of the active areas A233 in the X-direction. Also, the width of each of the active areas A323 in the X-direction is smaller than the width of each of the active areas A313 in the X-direction and is larger than the width of each of the active area A333 in the X-direction. It should be noted, however, that the difference in the width between any two of the active areas positioned adjacent to each other in the X-direction is within a predetermined range.

The width in the X-direction of each of the active areas included in each of the photodiode arrays 92c may keep decreasing in the X-direction from the end parts of the photodiode array 92c toward the center thereof. Alternatively, the width in the X-direction of each of the active areas included in each of the photodiode arrays may arrive at a minimum value before reaching the center of the photodiode array 92c from an end part of the photodiode array 92c in the X-direction and may thereafter increase. In another example, the width in the X-direction of each of the active areas included in each of the photodiode arrays 92c may arrive at a minimum value before reaching the center of the photodiode array 92c from an end part of the photodiode array in the X-direction, so that the widths of a predetermined number of photodiodes thereafter each exhibit the minimum value, before the width starts increasing thereafter.

Further, as illustrated in FIG. 12, the widths in the Y-direction of the active areas A113, the active areas A123, the active areas A133, and so on e equal to one another. Similarly, as illustrated in FIG. 12, the widths in the direction of the active areas A213, the active areas A223, the active areas A233, and so on are equal to one another. Also, as illustrated in FIG. 12, the widths in the Y-direction of the active areas A313, the active areas A323, the active areas A333, and so on are equal to one another.

The width in the Y-direction of each of the active areas included in each of the photodiode arrays 92c decreases in the Y-direction from the end parts of the photodiode array 92c toward the center thereof. For example, as illustrated in FIG. 12, the width of each of the active areas A213 in the Y-direction is smaller than the width of each of the active areas A113 in the Y-direction and is larger than the width of each of the active areas A313 in the Y-direction. Similarly, the width of each of the active areas A223 in the Y-direction is smaller than the width of each of the active areas A123 in the Y-direction and is larger than the width of each of the active areas A323 in the Y-direction. Also, the width of each of the active areas A233 in the Y-direction is smaller than the width of each of the active areas A133 in the Y-direction and is larger than the width of each of the active areas A333 in the Y-direction. It should be noted, however, that the difference in the width between any two of the active areas positioned adjacent to each other in the Y-direction is within a predetermined range.

The width in the Y-direction of each of the active areas included in each of the photodiode arrays 92c may keep decreasing in the Y-direction from the end parts of the photodiode array 92c toward the center thereof. Alternatively, the width in the Y-direction of each of the active areas included in each of the photodiode arrays 92c may arrive at a minimum value before reaching the center of the photodiode array 92c from an end part of the photodiode array 92c in the Y-direction and may thereafter increase. In another example, the width in the Y-direction of each of the active areas included in each of the photodiode arrays 92c may arrive at a minimum value before reaching the center of the photodiode array 92c from an end part of the photodiode array 92c in the Y-direction, so that the widths of a predetermined number of photodiodes thereafter each exhibit the minimum value, before the width starts increasing thereafter.

Further, as illustrated in FIG. 12, the widths in the X-direction of the active areas A113, the active areas A213, the active areas A313, and so on are equal to one another. Similarly, as illustrated in FIG. 12, the widths in the X-direction of the active areas A123, the active areas A223, the active areas A323, and so on are equal to one another. Also, as illustrated in FIG. 12, the widths in the X-direction of the active areas A133, the active areas A233, the active areas A333, and so on are equal to one another.

The interval in the X-direction between each pair of active areas included in each of the photodiode arrays 92c increases in the X-direction from the end parts of the photodiode array 92c toward the center thereof. For example, as illustrated in FIG. 12, the interval in the X-direction between the active area A123 and the active area A133 is larger than the interval in the X-direction between the active area A113 and the active area A123. Similarly, the interval in the X-direction between the active area A223 and the active area A233 is larger than the interval in the X-direction between the active area A213 and the active area A223. Also, the interval in the X-direction between the active area A323 and the active area A333 is larder than the interval in the X-direction between the active area A313 and the active area A323. In other words, the intervals between the pairs of active areas positioned adjacent to each other in the X-direction exhibit multiple values.

Further, as explained above, the width in the X-direction of each of the photodiodes included in each of the photodiode arrays 92c decreases in the X-direction from the end parts of the photodiode array 92c toward the center thereof. Accordingly, as explained above, it is possible to configure the X-ray detector 9c in such a manner that, as illustrated in FIG. 12, the width in the X-direction of each of the active areas included in each of the photodiode arrays 92c decreases from the end parts of the photodiode array 92c toward the center thereof.

The interval in the Y-direction between each pair of active areas included in each of the photodiode arrays 92c increases in the Y-direction from the end parts of the photodiode array 92c toward the center thereof. For example, as illustrated in FIG. 12, the interval in the Y-direction between the active area A210 and the active area A313 is larger than the interval in the Y-direction between the active area A113 and the active area A213. Similarly, the interval in the Y-direction between the active area A223 and the active area A323 is larger than the interval in the Y-direction between the active area A123 and the active area A223. Also, the interval in the Y-direction between the active area A233 and the active area A333 is larger than the interval in the Y-direction between the active area A133 and the active area A233. In other words, the intervals between the pairs of active areas positioned adjacent to each other in the Y-direction exhibit multiple values.

Further, as explained above, the width in the Y-direction of each of the photodiodes included in each of the photodiode arrays 92c decreases in the Y-direction from the end parts of the photodiode array 92c toward the center thereof. Accordingly, as explained above, it is possible to configure the X-ray detector 9c in such a manner that, as illustrated in FIG. 12, the width in the Y-direction of each of the active areas included in each of the photodiode arrays 92c decreases from the end parts of the photodiode array 92c toward the center thereof.

Figure 13:
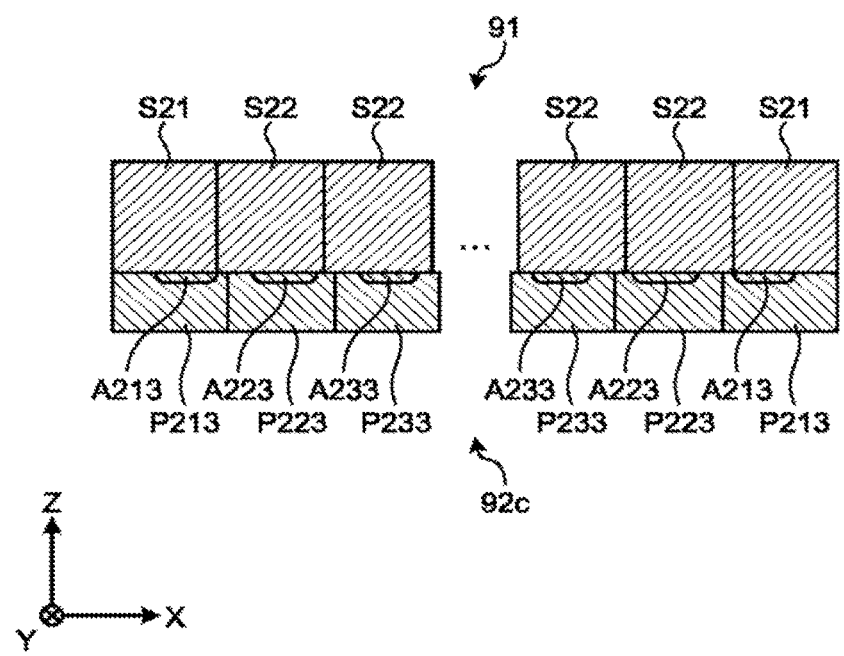
FIG. 13 is a cross-sectional view of one of the photodiode arrays illustrated in FIG. 12 and a scintillator array positioned on the +Z direction side of the photodiode array, being cross-sectioned by a plane that passes through active areas and is positioned parallel to the Z-X plane and being viewed from the −Y direction.
Figure 14:
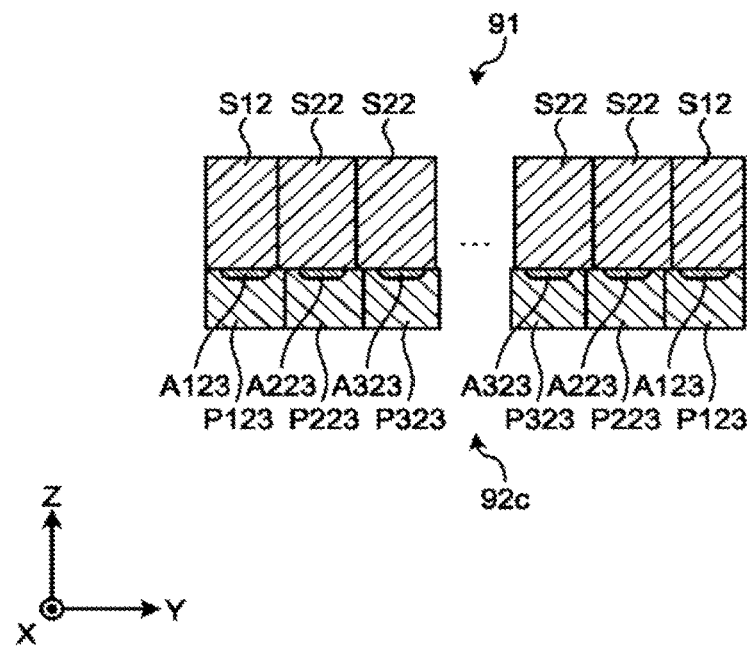
FIG. 14 is a cross-sectional view of the one of the photodiode arrays illustrated in FIG. 12 and the scintillator array positioned on the +Z direction side of the photodiode array, being cross-sectioned by a plane that passes through active areas and is positioned parallel to the Y-Z plane and being viewed from the +X direction.

Further, as illustrated in FIGS. 13 and 14, the scintillator array 91 is disposed on the side of the photodiode array 92c. As illustrated in FIG. 13, the sum of the widths in the X-direction of the two scintillators S21 and the plurality of scintillators S22 disposed therebetween is equal to the sum of the widths in the X-direction of the photodiode P213, the photodiode P223, the photodiode P233, . . . , the photodiode P233, the photodiode P223, and the photodiode P213. Further, as illustrated in FIG. 14, the sum of the widths in the Y-direction of the two scintillators S12 and the plurality of scintillators S22 disposed therebetween is equal to the sum of the widths in the Y-direction of the photodiode P123, the photodiode P223, the photodiode P323, ..., the photodiode P323, the photodiode P223, and the photodiode P123.

Further, as illustrated in FIGS. 13 and 14, each of the active areas included in each of the photodiode arrays 92c is covered by only one scintillator in the X-direction and the Y-direction. For example, as illustrated in FIGS. 13 and 14, each of the active areas A223 is covered by only one scintillator S22 in the X-direction and the Y-direction. Similarly, each of the active areas A233 is covered by only one scintillator S22 in the X-direction and the Y-direction. Also, each of the active areas A323 is covered by only one scintillator S22 in the X-direction and the Y-direction. Further, each of the active areas A213 is covered by only one scintillator S21 in the X-direction and the Y-direction. Furthermore, each of the active areas A123 is covered by only one scintillator S12 in the X-direction and the Y-direction.

As explained above, the X-ray detector 9c according to the third embodiment is configured in such a manner that the difference in the width between any two of the active areas positioned adjacent to each other in the first direction and the difference in the width between any two of the active areas positioned adjacent to each other in the second direction are within the predetermined range and that the intervals between the pairs of adjacently-positioned active areas exhibit multiple values. Further, the X-ray detector 9c according to the third embodiment is configured in such a manner that the width of each of the active areas decreases in the first direction and the second direction from the end parts of the photodiode array toward the center thereof. Consequently, similarly to the X-ray detector 9b according to the second embodiment, the X-ray detector 9c according to the third embodiment is able to suppress the occurrence of artifacts that may be caused by the detection efficiency levels or the SN ratios being different among the photodiodes. Further, similarly to the X-ray detector 9b according to the second embodiment, the X-ray detector 9c according to the third embodiment has fewer design constraints than the X-ray detector 9a according to the first embodiment.

Fourth Embodiment

An X-ray detector 9d according to a fourth embodiment will be explained. Further, some of the constituent elements that are the same as those in any of the embodiments described above will be referred to by using the same reference characters as those used in the description of the embodiment. Detailed explanations of some of the configurations that are duplicates of those in any of the embodiments described above will be omitted.

The X-ray detector 9d according to the fourth embodiment will be explained, with reference to FIGS. 15, 16, and 17. In the X-ray detector 9d, the widths of the active areas periodically varies in at least one selected from between the first direction and the second direction.

Figure 15:
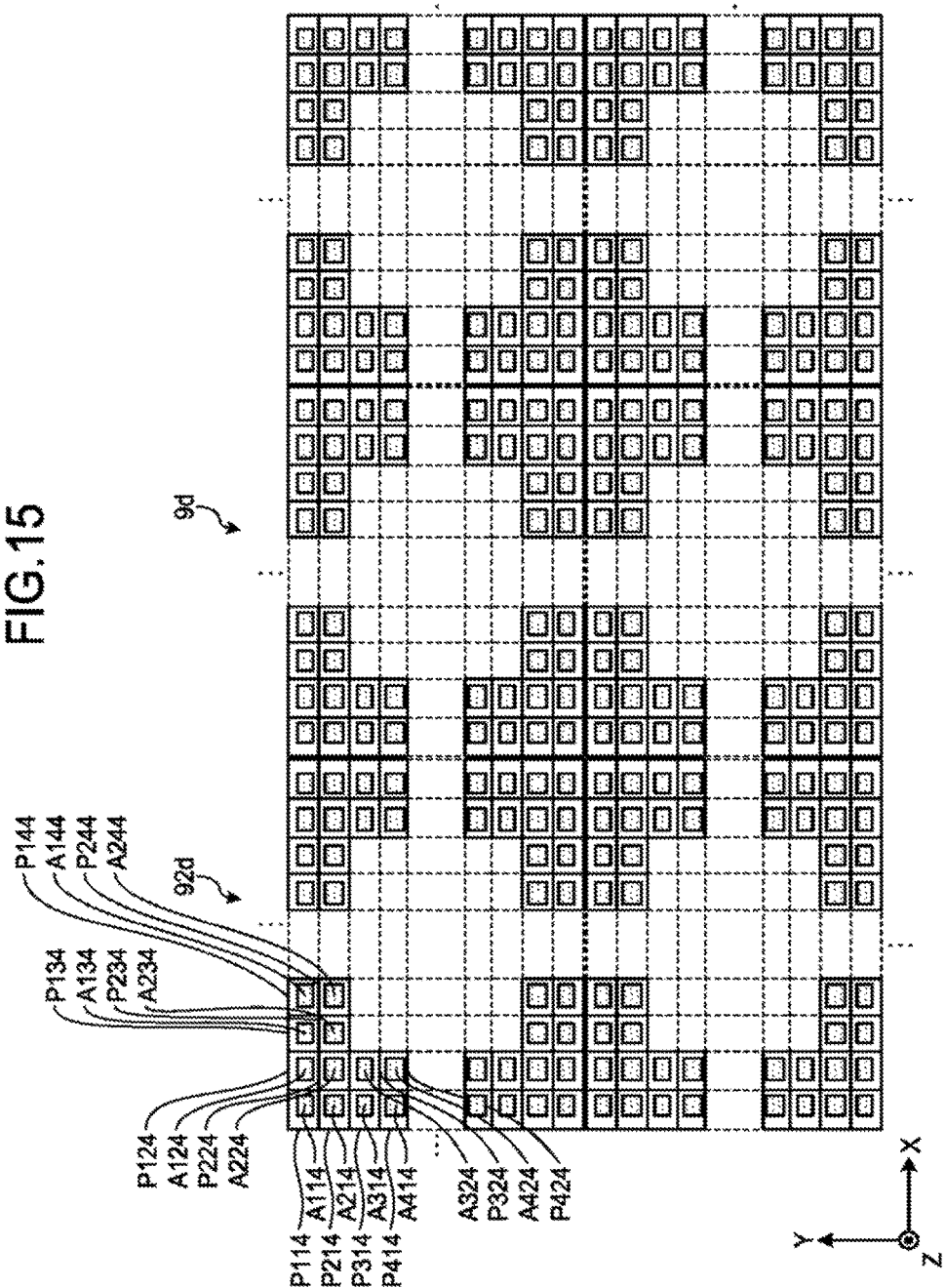
FIG. 15 is a drawing of an example of positional arrangements of the photodiodes and the active areas included in an X-ray detector according to a fourth embodiment.

FIG. 15 is a drawing of an example of positional arrangements of the photodiodes and the active areas included in an X-ray detector according to the fourth embodiment. FIG. 16 is a cross-sectional view of one of the photodiode arrays illustrated in FIG. 15 and a scintillator array positioned on the +Z direction side of the photodiode array, being cross-sectioned by a plane that passes through active areas and is positioned parallel to the Z-X plane and being viewed from the −Y direction. FIG. 17 is a cross-sectional view of the one of the photodiode arrays illustrated in FIG. 15 and the scintillator array positioned on the +Z direction side of the photodiode array, being cross-sectioned by a plane that passes through active areas and is positioned parallel to the Y-Z plane and being viewed from the +X direction.

As illustrated in FIG. 15, in the X-ray detector according to the fourth embodiment, photodiode arrays 92d are arranged at certain intervals in the X-direction and Y-direction.

Each of the photodiode arrays 92d includes a plurality of photodiodes. For example, as illustrated in FIG. 15, each of the photodiode arrays 92d includes photodiodes P114, photodiodes P124, photodiodes P134, photodiodes P144, photodiodes P214, photodiodes P224, photodiodes P234, photodiodes P244, photodiodes P314, photodiodes P324, photodiodes P414, and photodiodes P424.

The width in the X-direction of each of the photodiodes included in each of the photodiode arrays 92d decreases in the X-direction from the end parts of the photodiode array 92d toward the center thereof. For example, as illustrated in FIG. 15, in the first row of each of the photodiode arrays 92d, a photodiode P114, a photodiode P124, a photodiode P134, and a photodiode P144 are arranged from the end part toward the center. As illustrated in FIG. 15, the widths of the four photodiodes in the X-direction decrease in the order of the photodiode P114, the photodiode P124, the photodiode P134, and the photodiode P144.

Further, for example, as illustrated in FIG. 15, the widths in the Y-direction of the photodiodes P114, the photodiodes P124, the photodiodes P134, the photodiodes P144, and so on are equal to one another. Similarly, as illustrated in FIG. 15, the widths in the Y-direction of the photodiodes P214, the photodiodes P224, the photodiodes P234, the photodiodes P244, and so on are equal to one another. Also, the widths in the Y-direction of the photodiodes P314, the photodiodes P324, and so on are equal to one another. Further, the widths in the Y-direction of the photodiodes P414, the photodiodes P424, and so on are equal to one another.

The width in the Y-direction of each of the photodiodes included in each of the photodiode arrays 92d decreases in the Y-direction from the end parts of the photodiode array 92d toward the center thereof. For example, as illustrated in FIG. 15, in the first column of each of the photodiode arrays 92d, the photodiode P114, a photodiode P214, a photodiode P314, and a photodiode P414 are arranged from each of the end part toward the center. The widths of the four photodiodes in the Y-direction decrease in the order of the photodiode P114, the photodiode P214, the photodiode P314, and the photodiode P414.

Further, for example, as illustrated in FIG. 15, the widths in the X-direction of the photodiodes P114, the photodiodes P214, the photodiodes P314, the photodiodes P414, and so on are equal to one another. Similarly, as illustrated in FIG. 15, the widths in the X-direction of the photodiodes P124, the photodiodes P224, the photodiode P324, the photodiodes P424, and so on are equal to one another. Also, the widths in the X-direction of the photodiodes P134, the photodiodes P234, and so on are equal to one another. Further, the widths in the X-direction of the photodiodes P144, the photodiodes P244, and so on are equal to one another.

Each of the photodiodes included in each of the photodiode arrays 92d has an active area. For example, as illustrated in FIG. 15, each of the photodiodes P114 has an active area A114. Each of the photodiodes P124 has an active area A124. Each of the photodiodes P134 has an active area A134. Each of the photodiodes P144 has an active area A144. Each of the photodiodes P214 has an active area A214. Each of the photodiodes P224 has an active area A224. Each of the photodiodes P234 has an active area A234. Each of the photodiodes P244 has an active area A244. Each of the photodiodes P314 has an active area A314. Each of the photodiodes P324 has an active area A324. Each of the photodiodes P414 has an active area A414. Each of the photodiodes P424 has an active area A424.

The widths in the X-direction of the active areas included in each of the photodiode arrays 92*d* periodically vary in the X-direction. For example, as illustrated in FIG. 15, in the first row of each of the photodiode arrays 92*d*, an active area A114, an active area A124, an active area A134, and an active area A144 are arranged from the end part toward the center. The width of the active area A114 in the X-direction is equal to the width of the active area A134 in the X-direction. The width of the active area A124 in the X-direction is equal to the width of the active area A144 in the X-direction. The width of the active area A114 in the X-direction and the width of the active area A134 in the X-direction are smaller than the width of the active area A124 in the X-direction and the width of the active area A144 in the X-direction. It should be noted, however, that the difference in the width between any two of the active areas positioned adjacent to each other in the X-direction is within a predetermined range.

Further, for example, as illustrated in FIG. 15, the widths in the Y-direction of the active areas A114, the active areas A124, the active areas A134, the active areas A144, and so on are equal to one another. Similarly, the widths in the Y-direction of the active areas A214, the active areas A224, the active areas A234, the active areas A244, and so on are equal to one another. Also, the widths in the Y-direction of the active areas A314, A324, and so on are equal to one another. Further, the widths in the Y-direction of the active areas A414, A424, and so on are equal to one another.

The widths in the Y-direction of the active areas included in each of the photodiode arrays 92*d* periodically vary in the Y-direction. For example, as illustrated in FIG. 15, in the first column of each of the photodiode arrays 92*d*, the active area A114, an active area A214, an active area A314, and an active area A414 are arranged from the end part toward the center. The width of the active area A114 is the Y-direction is equal to the width of the active area A314 in the Y-direction. The width of the active area A214 in the Y-direction is equal to the width of the active area A414 in the Y-direction. The width of the active area A114 in the Y-direction and the width of the active area A314 in the Y-direction are smaller than the width of the active area A214 in the Y-direction and the width of the active area A414 in the Y-direction. It should be noted, however, that the difference in the width between any two of the active areas positioned adjacent to each other in the Y-direction is within a predetermined range.

Further, for example, as illustrated in FIG. 15, the widths in the X-direction of the active areas A114, the active areas A214, the active areas A314, the active areas A414, and so on are equal to one another. Similarly, the widths in the X-direction of the active areas A124, the active areas A224, the active areas A324, the active areas A424, and so on are equal to one another. Also, the widths in the X-direction of the active areas A134, the active areas A234, and so on are equal to one another. Further, the widths in the X-direction of the active areas A144, the active areas A244, and so on are equal to one another.

The interval in the X-direction between each pair of active areas included in each of the photodiode arrays 92*d* increases in the X-direction from the end parts of the photodiode array 92*d* toward the center thereof. For example, as illustrated in FIG. 15, the interval in the X-direction between the active area A124 and the active area A134 is larger than the interval in the X-direction between the active area A114 and the active area A124 and is smaller than the interval in the X-direction between the active area A134 and the active area A144. Similarly, the interval in the X-direction between the active area A224 and the active area A234 is larger than the interval in the X-direction between the active area A214 and the active area A224 and is smaller than the interval in the X-direction between the active area A234 and the active area A244. In other words, the intervals between the pairs of active areas positioned adjacent to each other in the X-direction exhibit multiple values.

Further, as explained above, the width in the X-direction of each of the photodiodes included in each of the photodiode arrays 92*d* decreases in the X-direction from the end parts of the photodiode array 92*d* toward the center thereof. Accordingly, as explained above, it is possible to configure the X-ray detector 9*d* in such a manner that, as illustrated in FIG. 15, the widths in the X-direction of the active areas included in each of the photodiode arrays 92*d* periodically vary in the X-direction.

The interval in the Y-direction between each pair of active areas included in each of the photodiode arrays 92*d* increases in the Y-direction from the end parts of the photodiode array 92*d* toward the center thereof. For example, as illustrated in FIG. 15, the interval in the Y-direction between the active area A214 and the active area A314 is larger than the interval in the Y-direction between the active area A114 and the active area A214 and is smaller than the interval in the Y-direction between the active area A314 and the active area A414. Similarly, the interval in the Y-direction between the active area A224 and the active area A324 is larger than the interval in the Y-direction between the active area A124 and the active area A224 and is smaller than the interval in the Y-direction between the active area A324 and the active area A424. In other words, the intervals between the pairs of active areas positioned adjacent to each other in the Y-direction exhibit multiple values.

Further, as explained above, the width in the Y-direction of each of the photodiodes included in each of the photodiode arrays 92*d* decreases in the Y-direction from the end parts of the photodiode array 92*d* toward the center thereof. Accordingly, as explained above, it is possible to configure the X-ray detector 9*d* in such a manner that, as illustrated in FIG. 15, the widths in the Y-direction of the active areas included in each of the photodiode arrays 92*d* periodically vary in the Y-direction.

Figure 16:
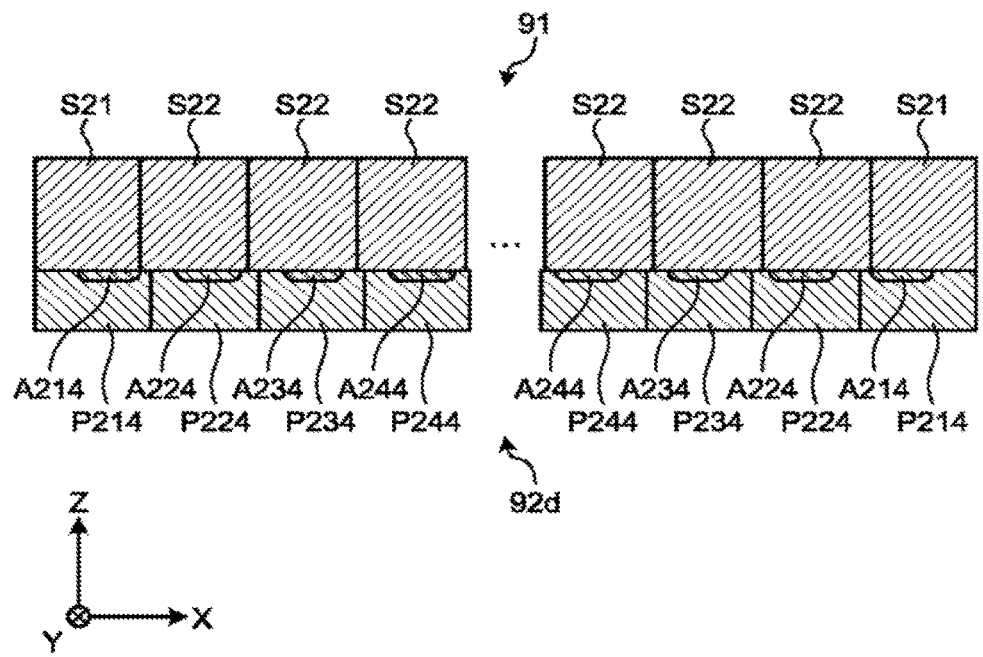
FIG. 16 is a cross-sectional view of one of the photodiode arrays illustrated in FIG. 15 and a scintillator array positioned on the +Z direction side of the photodiode array, being cross-sectioned by a plane that passes through active areas and is positioned parallel to the Z-X plane an being viewed from the −Y direction.
Figure 17:
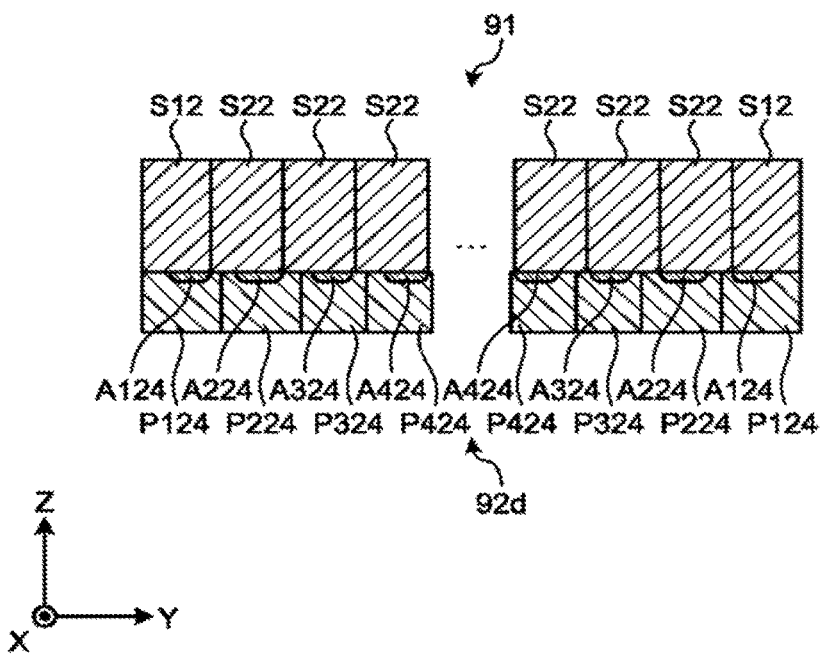
FIG. 17 is a cross-sectional view of the one of the photodiode arrays illustrated in FIG. 15 and the scintillator array positioned on the +Z direction side of the photodiode array, being cross-sectioned by a plane that passes through active areas and is positioned parallel to the Y-Z plane an being viewed from the +X direction.

Further, as illustrated in FIGS. 16 and 17, the scintillator array 91 is disposed on the +Z direction side of the photodiode array 92*d*. As illustrated in FIG. 16, the sum of the widths in the X-direction of the two scintillators S21 and the plurality of scintillators S22 disposed therebetween is equal to the sum of the widths in the X-direction of the photodiode P214, the photodiode P224, the photodiode P234, the photodiode P244, . . . , the photodiode P244, the photodiode P234, the photodiode P224, and the photodiode P214. Further, as illustrated in FIG. 17, the sum of the widths in the Y-direction of the two scintillators S12 and the plurality of scintillators S22 disposed therebetween is equal to the sum of the widths in the Y-direction of the photodiode P124, the photodiode P224, the photodiode P324, the photodiode P424, . . . , the photodiode P424, the photodiode P324, the photodiode P224, and the photodiode P124.

Further, as illustrated in FIGS. 16 and 17, each of the active areas included in each of the photodiode arrays 92*d* is covered by only one scintillator in the X-direction and the Y-direction. For example, as illustrated in FIGS. 16 and 17, each of the active areas A224 is covered by only one scintillator S22 in the X-direction and the Y-direction. Similarly, each of the active areas A234, the active areas A244, the active areas A324, and the active areas A424 is covered by only one scintillator S22 in the X-direction and the Y-direction. Also, each of the active areas A214 is covered by only one scintillator S21 in the X-direction and the Y-direction. Further, each of the active areas A124 is covered by only one scintillator S12 in the X-direction and the Y-direction.

As explained above, the X-ray detector 9d according to the fourth embodiment is configured in such a manner that the difference in the width between any two of the active areas positioned adjacent to each other in the first direction and the difference in the width between any two of the active areas positioned adjacent to each ether in the second direction are within the predetermined range and that the intervals between the pairs of adjacently-positioned active areas exhibit multiple values. Further, the X-ray detector 9d according to the fourth embodiment is configured in such a manner that the widths of the active areas periodically vary in the first direction and the second direction. Consequently, similarly to the X-ray detector 9b according to the second embodiment, the X-ray detector 9d according to the fourth embodiment is able to suppress the occurrence of artifacts that may be caused by the detection efficiency levels or the SN ratios being different among the photodiodes. Further, similarly to the X-ray detector 9b according to the second embodiment, the X-ray detector 9d according to the fourth embodiment has fewer design constraints than the X-ray detector 9a according to the first embodiment.

Furthermore, in the X-ray detector 9d according to the fourth embodiment, it is easier to narrow the widths of the active areas positioned at the end parts of each of the photodiode arrays. Consequently, it is possible to more easily realize the X-ray detector 9d according to the fourth embodiment than the X-ray detector 9a according to the first embodiment.

Fifth Embodiment

An X-ray detector 9e according to a fifth embodiment will be explained. Further, some of the constituent elements that are the same as those in any of the embodiments described above will be referred to by using the same reference characters as those used in the description of the embodiment. Detailed explanations of some of the configurations that are duplicates of those in any of the embodiments described above will be omitted.

Figure 18:
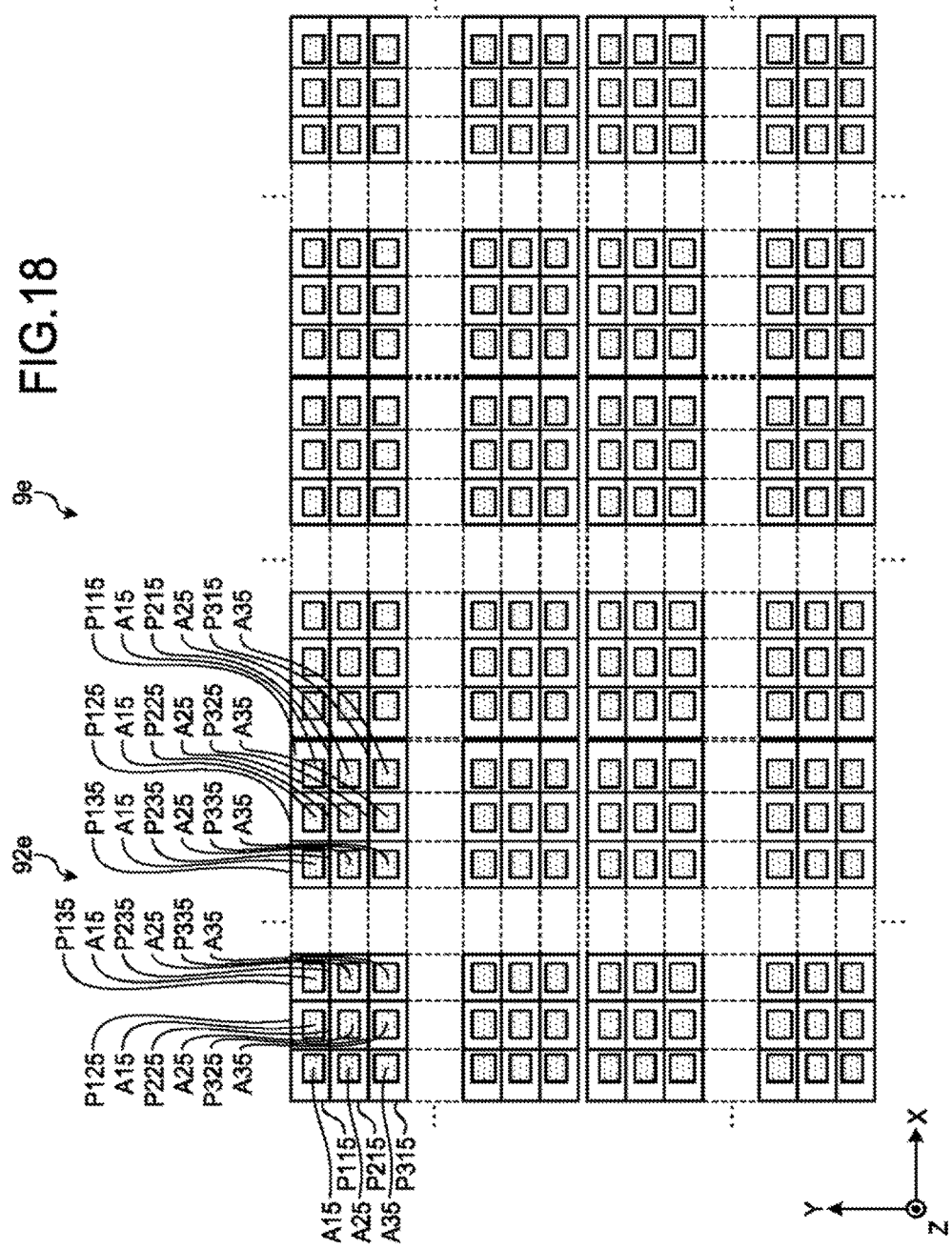
FIG. 18 is a drawing of an example of positional arrangements of photodiodes and active areas included in an X-ray detector according to a fifth embodiment.

The X-ray detector 9e according to the fifth embodiment will be explained with reference to FIG. 18. The X-ray detector 9e is configured in such a manner that the widths of the active areas in the first direction are equal to one another similarly to the first embodiment and that the width in the second direction of each of the active areas increases from the end parts of the photodiode array toward the center thereof similarly to the second embodiment. FIG. 18 is a drawing of an example of positional arrangements of photodiodes and active areas included in an X-ray detector according to the fifth embodiment.

As illustrated in FIG. 18, in the X-ray detector 9e according to the fifth embodiment, photodiode arrays 92e are arranged at certain intervals in the X-direction and Y-direction.

Each of the photodiode arrays 92e includes a plurality of photodiodes. For example, as illustrated in FIG. 13, each of the photodiode arrays 92e includes photodiodes P115, photodiodes P125, photodiodes P135, photodiodes P215, photodiodes P225, photodiodes P235, photodiodes P315, photodiodes P325, and photodiodes P335.

The width of each of these photodiodes in the X-direction decreases in the X-direction from the end parts of the photodiode array 92e toward the center thereof. For example, as illustrated in FIG. 18, the width of each of the photodiodes P125 in the X-direction is smaller than the width of each of the photodiodes P115 in the X-direction and is larger than the width of each of the photodiodes P135 in the X-direction. Similarly, the width of each of the photodiodes P225 in the X-direction is smaller than the width of each of the photodiodes P215 in the X-direction and is larger than the width of each of the photodiodes P235 in the X-direction. Also, the width of each of the photodiodes P325 in the X-direction is smaller than the width of each of the photodiodes P315 in the X-direction and is larger than the width of each of the photodiodes P335 in the X-direction.

Further, as illustrated in FIG. 18, the widths of the photodiodes P115, the photodiodes P125, the photodiodes P135, and so on in the Y-direction are equal to one another. Similarly, as illustrated in FIG. 18, the widths of the photodiodes P215, the photodiodes P225, the photodiodes P235, and so on in the Y-direction are equal to one another. Also, as illustrated in FIG. 18, the widths of the photodiodes P315, the photodiodes P325, the photodiodes P335, and so on in the Y-direction are equal to one another.

The width in the Y-direction of each of the photodiodes included in each of the photodiode arrays 92e decreases in the Y-direction from the end parts of the photodiode array 92e toward the center thereof. For example, as illustrated in FIG. 18, the width of each of the photodiodes P215 in the Y-direction is smaller than the width of each of the photodiodes P115 in the Y-direction and is larger than the width of each of the photodiodes P315 in the Y-direction. Similarly, the width of each of the photodiodes P225 in the Y-direction is smaller than the width of each of the photodiodes P125 in the Y-direction and is larger than the width of each of the photodiodes P325 in the Y-direction. Also, the width of each of the photodiodes P235 in the Y-direction is smaller than the width of each of the photodiodes P135 in the Y-direction and is larger than the width of each of the photodiodes P335 in the Y-direction.

Further, as illustrated in FIG. 18, the widths of the photodiodes P115, the photodiodes P215, the photodiodes P315, and so on in the X-direction are equal to one another. Similarly, as illustrated in FIG. 18, the widths of the photodiodes P125, the photodiodes P225, the photodiodes P325, and so on in the X-direction are equal to one another. Further, as illustrated in FIG. 18, the widths of the photodiodes P135, the photodiodes P235, the photodiodes P335, and so on in the X-direction are equal to one another.

Each of the photodiodes included in each of the photodiode arrays 92e has an active area. For example, as illustrated in FIG. 18, each of the photodiodes P115, the photodiodes P125, and the photodiodes P135 has an active area A15. Similarly, each of the photodiodes P215, the photodiodes P225, and the photodiodes P235 has an active area A25. Also, each of the photodiodes P315, the photodiodes P325, and the photodiodes P335 has an active area A35. In other words, the difference in the width between any two of the active areas positioned adjacent to each other in the X-direction is zero, while the difference in the width between any two of the active areas positioned adjacent to each other in the Y-direction is within a predetermined range.

The interval in the X-direction between each pair of active areas included in each of the photodiode arrays 92e increases in the X-direction from the end parts of the photodiode array 92e toward the center thereof. In other words, the intervals between the pairs of active areas positioned adjacent to each other in the X-direction exhibit multiple values. In this situation, the expression "the interval in the X-direction between each pair of active areas" denotes the distance between the centers of each pair of adjacently-positioned active areas in the X-direction. Further, as explained above, the width in the X-direction of each of the photodiodes included in each of the photodiode arrays 92e decreases in the X-direction from the end parts of the photodiode array 92e toward the center thereof. Accordingly, as illustrated in FIG. 18, it is possible to configure the X-ray detector 9e in such a manner that the widths in the X-direction of all the active areas included in the photodiode arrays 92e are equal to one another.

The interval in the Y-direction between each pair of active areas included in each of the photodiode arrays 92e increases in the Y-direction from the end parts of the photodiode array 92e toward the center thereof. In this situation, the expression "the interval in the Y-direction between each pair of active areas" denotes the distance between the centers of each pair of adjacently-positioned active areas in the Y-direction. For example, as illustrated in FIG. 18, the interval in the Y-direction between the active area A215 and the active area A315 is larger than the interval in the Y-direction between the active area A115 and the active area A215. Similarly, the interval in the Y-direction between the active area A225 and the active area A325 is larger than the interval in the Y-direction between the active area A125 and the active area A225. Also, the interval in the Y-direction between the active area A235 and the active area A335 is larger than the interval in the Y-direction between the active area A135 and the active area A235. In other words, the intervals between the pairs of active areas positioned adjacent to each other in the Y-direction exhibit multiple values.

Further, as explained above, the width in the Y-direction of each of the photodiodes included in each of the photodiode arrays 92e decreases in the Y-direction from the end parts of the photodiode array 92e toward the center thereof. Accordingly, as explained above, it is possible to configure the X-ray detector 9e in such a manner that, as illustrated in FIG. 18, the width in the Y-direction of each of the active areas included in each of the photodiode arrays 92e increases from the end parts of the photodiode array 92e toward the center thereof.

As explained above, the X-ray detector 9e according to the fifth embodiment is configured in such a manner that the difference in the width between any two of the active areas positioned adjacent to each other in the first direction is zero, while the difference in the width between any two of the active areas positioned adjacent to each other in the second direction is within the predetermined range and that the intervals between the pairs of adjacently-positioned active areas exhibit multiple values. Further, the X-ray detector 9e according to the fifth embodiment is configured in such a manner that the widths of the active areas in the first direction are equal to one another, while the width of each of the active areas in the second direction increases from the end parts of the photodiode array 92e toward the center thereof. Accordingly, the X-ray detector 9e according to the fifth embodiment achieves, in the first direction, the same advantageous effects as those achieved by the X-ray detector 9a according to the first embodiment and further achieves, in the second direction, the same advantageous effects as those achieved by the X-ray detector 9b according to the second embodiment.

In the fifth embodiment, the example is explained in which the width of the active areas are equal to one another in the first direction similarly to the first embodiment, while the width of each of the active areas in the second direction increases from the end parts of the photodiode array 92e toward the center thereof similarly to the second embodiment; however, possible embodiments are not limited to this example. It is possible to arbitrary choose a combination of a variation in the widths of the active areas in the first direction and a variation in the widths of the active areas in the second direction.

Further, in the embodiments described above, the examples are explained in which, within each of the photodiode arrays, at least one selected from among the following varies: the widths of the photodiodes, the differences in the width among the active areas, the intervals between the pairs of active areas positioned adjacent to each other, and the widths of the active areas; however, possible embodiments are not limited to these examples. For instance, another arrangement is acceptable in which, among a plurality of photodiode arrays, at least one selected from among the following varies: the widths of the photodiodes, the differences in the width among the active areas, the intervals between the pairs of active areas positioned adjacent to each other, and the widths of the active areas. Alternatively, yet another arrangement is acceptable in which, throughout the X-ray detector, at least one selected from among the following varies: the widths of the photodiodes, the differences in the width among the active areas, the intervals between the pairs of active areas positioned adjacent to each other, and the widths of the active areas.

The processor explained above may be, for example, a Central Processing Unit (CPU), a Graphics Processing Unit (GPU), an Application Specific Integrated Circuit (ASIC), a Programmable Logic Device (PLD), or a Field Programmable Gate Array (FPGA). The Programmable Logic Device (PLD) may be, for example, a Simple Programmable Logic Device (SPLD) or a Complex Programmable Logic Device (CPLD).

In the embodiments described above, the high-voltage generating circuitry 3, the collimator adjusting circuitry 4, the gantry driving circuitry 5, the data acquiring circuitry 10, the couch driving circuitry 22, and the processing circuitry 46 each realize the functions thereof by reading and executing the corresponding program stored in the storage circuitry 45; however, possible embodiments are not limited to this example. It is also acceptable to have the corresponding program directly incorporated in each circuitry, instead of having the programs stored in the storage circuitry 45. In that situation, each circuitry realizes the functions thereof by reading and executing the program directly incorporated therein.

The sets of circuitry illustrated in FIG. 1 may be distributed or integrated together as necessary. For example, the processing circuitry 46 may be distributed into scar controlling circuitry, pre-processing circuitry, image generating circuitry, display controlling circuitry, and controlling circuitry configured to execute the functions of the scan controlling function 461, the pre-processing function 462, the image generating function 463, the display controlling function 464, and the controlling function 465, respectively. Further, it is also acceptable to arbitrarily integrate together any of the following: the high-voltage generating circuitry 3, the collimator adjusting circuitry 4, the gantry driving circuitry 5, the data acquiring circuitry 10, the couch driving circuitry 22, and the processing circuitry 46.

According to at least one aspect of the embodiments described above, it is possible to provide an X-ray detector and an X-ray CY apparatus that are able to suppress the occurrence of artifacts by improving the detection efficiency levels and the SN ratios of the photodiodes.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray detector, comprising:
a scintillator array in which a plurality of scintillators are arranged in a first direction and a second direction intersecting the first direction; and
a photodiode array including photodiodes, each of which is installed for a different one of the scintillators and each of which has an active area configured to convert visible light emitted by the scintillator into an electrical signal, wherein
the photodiodes in the photodiode array are arranged in such a manner that widths of the active areas in the first direction are equal to one another; and
widths of the active areas in the second direction increase from an end part of the photodiode array toward a center thereof.

2. An X-ray CT apparatus, comprising:
an X-ray tube that radiates X-rays onto a subject; and
an X-ray detector that includes a scintillator array in which a plurality of scintillators configured to convert the X-rays into visible light are arranged in a first direction and a second direction intersecting the first direction and a photodiode array including photodiodes each of which is installed for a different one of the scintillators and each of which has an active area configured to convert the visible light into an electrical signal, wherein
the photodiodes are arranged in such a manner that widths of the active areas in the first direction are equal to one another, while a difference in the width between any two of the active areas positioned adjacent to each other in the second direction is within a predetermined range; and
widths of the active areas in the second direction increase from an end part of the photodiode array toward a center thereof.

3. An X-ray detector, comprising:
a scintillator array in which a plurality of scintillators are arranged in a first direction and a second direction intersecting the first direction; and
a photodiode array including photodiodes, each of which is installed for a different one of the scintillators and each of which has an active area configured to convert visible light emitted by the scintillator into an electrical signal, wherein
the photodiodes in the photodiode array are arranged in such a manner that widths of the active areas in the first direction are equal to one another;
widths of the photodiodes in the first direction decrease from an end part of the photodiode array toward a center thereof; and
widths of the active areas in the second direction increase from an end part of the photodiode array toward a center thereof.

* * * * *